United States Patent [19]

Chandrakumar et al.

[11] Patent Number: 5,420,270

[45] Date of Patent: May 30, 1995

[54] ARYL SUBSTITUTED DIBENZOXAZEPINE COMPOUNDS, PHARMACEUTICAL COMPOSITIONS AND METHODS OF USE

[75] Inventors: Nizal S. Chandrakumar, Vernon Hills, Ill.; Horng-Chih Huang, Chesterfield, Mo.; Richard A. Mueller, Glencoe, Ill.

[73] Assignee: G. D. Searle & Co., Chicago, Ill.

[21] Appl. No.: 133,681

[22] Filed: Oct. 7, 1993

[51] Int. Cl.⁶ .................. C07D 281/14; A61K 31/55
[52] U.S. Cl. ................................................ 540/488
[58] Field of Search ............................................ 340/488

[56] References Cited

U.S. PATENT DOCUMENTS

| | | | |
|---|---|---|---|
| 2,852,528 | 9/1958 | Hoffmann et al. | 260/327 |
| 3,210,372 | 10/1965 | Werner et al. | 260/309.6 |
| 3,357,998 | 12/1967 | Cusic et al. | 260/333 |
| 3,534,019 | 10/1970 | Coyne et al. | 260/239 |
| 3,624,104 | 11/1971 | Cusic et al. | 260/333 |
| 3,917,649 | 11/1975 | Mueller | 260/333 |
| 3,989,719 | 11/1976 | Mueller | 260/333 |
| 3,992,375 | 11/1976 | Mueller | 260/240 |
| 4,045,442 | 8/1977 | Mueller | 260/293.58 |
| 4,125,532 | 11/1978 | Mueller | 260/244.4 |
| 4,170,593 | 10/1979 | Mueller | 260/243.3 |
| 4,290,953 | 9/1981 | Koizumi et al. | 260/333 |
| 4,360,525 | 11/1982 | Müller | 424/267 |
| 4,379,150 | 4/1983 | Ito et al. | 424/244 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,681,939 | 7/1904 | Mueller | 540/547 |
| 4,704,386 | 11/1987 | Mueller | 514/211 |
| 4,888,335 | 12/1989 | Mohrbacher et al. | 514/217 |
| 5,180,720 | 1/1993 | Husa et al. | 514/211 |
| 5,182,272 | 1/1993 | Hallinan et al. | 514/211 |
| 5,189,033 | 2/1993 | Tucker | 540/488 |
| 5,212,169 | 5/1993 | Husa et al. | 514/211 |
| 5,311,101 | 5/1994 | Oldfield et al. | 540/488 |

FOREIGN PATENT DOCUMENTS

| | | | |
|---|---|---|---|
| 0012385 | 6/1980 | European Pat. Off. | C07D 267/20 |
| 0193822 | 9/1986 | European Pat. Off. | C07D 267/20 |
| 0218077 | 4/1987 | European Pat. Off. | C07D 267/20 |
| 0480641 | 4/1992 | European Pat. Off. | C07D 223/20 |
| 0534667 | 3/1993 | European Pat. Off. | C07D 417/06 |
| 6700603 | 7/1967 | Netherlands . | |
| 1170322 | 11/1969 | United Kingdom | C07D 87/54 |
| 1331892 | 9/1973 | United Kingdom | C07D 87/54 |
| 1522003 | 8/1978 | United Kingdom | C07I 267/20 |

OTHER PUBLICATIONS

A. Bennett et al. "Antagonism of Prostanoid-Induced Contractions of Rat Gastric Fundus Muscle by SC-19220 Sodium Meclofenamate, Indomethacin or Trimethoquinol," Br. J. Pharmac., 71, 169–175 (1980)--London.

(List continued on next page.)

*Primary Examiner*—Robert T. Bond
*Attorney, Agent, or Firm*—Roberta L. Hastreiter; Roger A. Williams

[57] ABSTRACT

The present invention provides substituted dibenzoxazepine compounds of Formula I:

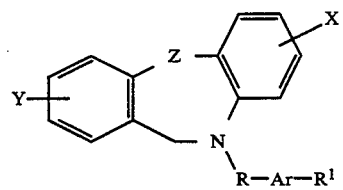

which are useful as analgesic agents for the treatment of pain, and for the treatment of prostaglandin $E_2$-mediated diseases, pharmaceutical compositions comprising a therapeutically-effective amount of a compound of Formula I in combination with a pharmaceutically-acceptable carrier, a method for eliminating or ameliorating pain in an animal, and a method for treating prostaglandin $E_2$-mediated diseases in an animal, comprising administering a therapeutically-effective amount of a compound of Formula I to the animal.

18 Claims, No Drawings

OTHER PUBLICATIONS

S. Nakajyo, et al. "Inhibitory Effect of Bassianolide, a Cyclodepsipeptide, on Drug-Induced Contractions of Isolated Smooth Muscle Preparations," *Japan J. Pharmacol.*, 32, 55–64 (1982)–Japan.

A. Rakovska, et al. "Antagonistic Effect of SC-19220 on the Responses of Guinea-Pig Gastric Muscles to Prostaglandins $E_1$, $E_2$, and $F_{2\alpha}$'," *Arch. Int. Pharmacodyn.*, 268, 59–69 (1984)–USA.

J. H. Sanner "Dibenzoxazepine Hydrazides as Prostaglandin Antagonists," *Intra-Science Chem. Rept.*, vol. 6, No. 1, 1–9 (1972)–USA.

J. H. Sanner, et al. "Structure-Activity Relationships of Some Dibenzoxazepine Derivatives as Prostaglandin Antagonists," *Advances in the Biosciences*, 9, 139–148 (1972)–USA.

W. E. Coyne, et al. "Anticonvulsant Semicarbazides," *J. Med. Chem.*, 11(6), 1158–1160 (1968)–USA.

E. J. Drower, et al. "The Antiociceptive Effects of Prostaglandin Antagonists in the Rat," *European Journal of Pharmacology*, 133, 249–256 (1987)–Europe.

F. R. George, et al. "Antafonism of Alcohol Hypnosis by Blockade of Prostaglandin Synthesis and Activity: Genotype and Time Course Effects," *Pharmacology, Biochemistry & Behavior*, vol. 19, 131–136 (1983)–USA.

R. Gimet, et al. "Quantitative Determination of Polymorphic Forms in a Formulation Matrix using the Near Infra-Red Reflectance Analysis Technique," *Journal of Pharmaceutical & Biomedical Analysis*, vol. 5, No. 3, 205–211 (1987)–Great Britain.

A. Gomes, et al. "Pharmacodynamics of Venom of the Centipede *Scolopendra subspinipes dehaani*," *Indian Journal of Experimental Biology*, vol. 20, 615–618, Aug. (1982)–India.

K. Gyires, et al. "The Use of the Writhing Test in Mice for Screening Different Types of Analgesics," *Arch. Int. Pharmacodyn*, 267, 131–140 (1984)–USA.

D. E. MacIntyre, et al. "Antagonism of Human Platelet Responses to Stimulatory and Inhibitory Prostaglandins," *Prog. Lipid. Res.*, 20 (1–4), 453–9 (1981)–USA.

C. A. Maggi, et al. "The Effect of SC-19220, a Prostaglandin Antagonist, on the Micturition Reflex in Rats," *European Journal of Pharmacology*, 152, 273–279 (1988)–Europe.

K. Nagarajan, et al. "Synthesis of 10,11-Dihydrodibenz[b,f][1,4]oxazepine Derivatives as Potential Anticonvulsant & Psychotropic Agents," *Indian Journal of Chemistry*, vol. 24B, 840–844 (1985)–India.

ARYL SUBSTITUTED DIBENZOXAZEPINE COMPOUNDS, PHARMACEUTICAL COMPOSITIONS AND METHODS OF USE

BACKGROUND OF THE INVENTION

1. Field of the Invention

The present invention generally relates to compounds having pharmacological activity which are useful as pharmaceutical agents and, more particularly, as analgesic agents for the treatment of pain, and as agents for the treatment of prostaglandin-$E_2$ mediated diseases, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain and prostaglandin-$E_2$ mediated diseases employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates Although the efficacy of opiates in relieving pain is well established, the associated addiction liability of opiates is a distinct disadvantage of these compounds.

While salicylate and salicylate-like agents (nonsteroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

2. Description of the Related Art

U.S. Pat. No. 3,624,104 discloses aralkanoyl derivatives of dibenzoxazepine-N-carboxylic acid hydrazide compounds.

U.S. Pat. No. 3,917,649 discloses dibenzoxazepine N-carboxylic acid hydrazine compounds.

U.S. Pat. No. 4,290,953 discloses dibenz[b,f][1,4]oxazepine derivatives.

U.S. Pat. No. 4,045,442 disclose 1-(substituted amino-)alkanoyl-2-(dibenzoxazepine-10-carbonyl)hydrazine compounds.

U.S. Pat. No. 4,379,150 discloses dibenz[b,f][1,4]oxazepine derivatives which may have a heterocyclic ring in the side chain at the 10-position of the compounds.

U.S. Pat. No. 4,681,939 discloses 8-chlorodibenz[b,f][1,4]-oxazepine-10(11H)-carboxylic acid, 2-[(substituted phenylsulfinyl)alkanoyl]-hydrazides and 8-chlorodibenz[b,f][1,4]oxazepine-10(11H)-carboxylic acid, 2-[(substituted phenylsulfonyl)alkanoyl]hydrazides.

U.S. Pat. No. 4,704,386 discloses 8-chlorodibenz[b,f][1,4]-oxazepine-10(11H)-carboxylic acid, 2-[(substituted phenylsulfinyl)alkanoyl]hydrazides and 8-chlorodibenz[b,f][1,4]oxazepine-10(11H)-carboxylic acid, 2-[(substituted phenylsulfonyl)alkanoyl]hydrazides.

U.K. Patent No. 1,522,003 discloses 1-acyl-2-(8-chloro-10,11-dihydrodibenz[b,f][1,4]oxazepine-10-carbonyl)hydrazines.

U.K. Patent No. 1,331,892 discloses dibenzoxazepine N-carboxylic acid hydrazides.

U.S. Pat. No. 4,888,335 discloses 3-alkoxy-2-aminopropyl heterocyclic amines.

U.S. Pat. No. 4,360,525 discloses 10-(4-piperidinyl)-10,11-dihydro-dibenz-[b,f][1,4]-oxazepines, -dibenzo[b,f][1,4]thiazepines and -5H-dibenzo[b,e][1,4]diazepines.

European Patent Application Publication No. 0 480 641 A1 discloses tricyclic heterocycles which may contain unsubstituted or substituted phenylene in the side chain at the 10-position of the compounds.

European Patent Application Publication No. 0 534 667 A1 discloses substituted tricyclic heterocycles which contain a heteroaryl group in the side chain at the 10-position of the compounds.

European Patent Application Publication No. 0 218 077 discloses 8-chlorodibenz[b,f][1,4]oxazepine10(11H)-carboxylic acid, 2-[-(substituted phenylsulfinyl)alkanoyl]hydrazide compounds and 8-chlorodibenz[b,f][1,4]oxazepine-10(11H)-carboxylic acid, 2-[(substituted phenylsulfonyl)alkanoyl]hydrazide compounds, and intermediates used in the preparation of these compounds.

J. H. Sanner, "Dibenzoxazepine Hydrazides as Prostaglandin Antagonists," Intra-Science Chem. Rept., 6(1), 1–9 (1972), describes experiments performed with two dibenzoxazepine derivatives designated SC-18637 and SC-19220, and found that SC-18637 and SC-19220 inhibit the stimulant actions of prostaglandins on isolated smooth muscle preparations.

Each of the documents described hereinabove discloses compounds which are structurally different from the compounds of the present invention. The compounds of the present invention are structurally distinct from that which has been described in the art.

SUMMARY OF THE INVENTION

The present invention provides compounds having a structure of Formula I:

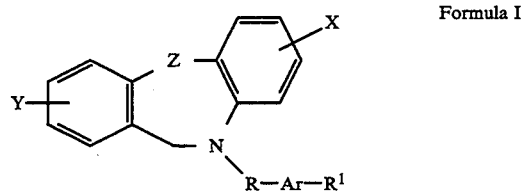

Formula I or a pharmaceutically-acceptable salt thereof, wherein:
X is hydrogen, halogen or —$CF_3$;
Y is hydrogen or halogen;
Z is oxygen, sulfur,

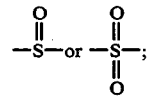

R is

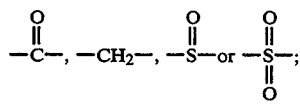

Ar is aryl; and

R$^1$ is hydrogen, halogen, aryl, alkylaryl, alkenylaryl, alkynylaryl, carboxy, carbonylalkoxy or carbonylaminoalkylaryl, with the proviso that R is not —CH$_2$— when R$^1$ is carboxy, phenyl or alkylphenyl.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal, or for treating prostaglandin-E$_2$ mediated diseases in an animal, comprising administering a therapeutically-effective amount of a compound of Formula I to the animal.

DETAILED DESCRIPTION OF THE INVENTION (1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes one, two or three carbon atoms, which can be a straight or branched chain. Representative of such radicals are methyl, ethyl, propyl, isopropyl, butyl, sec-butyl, isobutyl, tert-butyl, pentyl and the like.

The term "alkylaryl" as used herein means an alkyl group, as defined above, which has an aryl group, as defined below, attached thereto.

The term "alkenyl" as used herein means a hydrocarbon radical having from one to ten carbon atoms, within which includes from one to six carbon atoms, and further within which includes from one to three carbon atoms, which can be a straight or branched chain, and which includes one, two or three —CH=CH— groups.

The term "alkenylaryl" as used herein means an alkenyl group, as defined above, which has an aryl group, as defined below, attached thereto.

The term "alkynyl" as used herein means a hydrocarbon radical having from one to ten carbon atoms, within which includes from one to six carbon atoms, and further within which includes from one to three carbon atoms, which can be a straight or branched chain, and which includes one, two or three —CH=CH— groups.

The term "alkynylaryl" as used herein means an alkynyl group, as defined above, which has an aryl group, as defined below, attached thereto.

The term "alkoxy" as used herein means an alkyl radical, as defined above, having an oxygen atom attached thereto. Representative alkoxy groups include methoxy, ethoxy, propoxy, tert-butoxy and the like.

The abbreviation "AlMe$_3$" as used herein means trimethylaluminum.

The term "amino" as used herein means an —NH$_2$ group.

The term "aminoalkylaryl" as used herein means an amino group, as defined above, which has an alkylaryl group, as defined above, attached thereto.

The term "analgesia" as used herein means the reduction, or absence, of sensibility to pain, designating particularly the relief of pain without loss of consciousness.

The term "animal" as used herein includes mammals and nonmammals, and further includes humans and nonhuman mammals.

The term "aryl" as used herein means 5- or 6-membered single-ring aromatic radicals which may include from zero to four heteroatoms, such as nitrogen, sulfur and/or oxygen, within which includes from zero to two heteroatoms, and further within which includes from zero to one heteroatom. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "Boc" as used herein means t-butyloxycarbonyl.

The term "carbonyl" as used herein means a

group.

The term "carbonylalkoxy" as used herein means the group

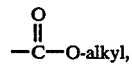

wherein alkyl is as defined above.

The term "carbonylamino" as used herein means the group

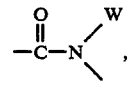

wherein W is hydrogen or alkyl, and wherein alkyl is as defined above.

The term "carbonylaminoalkylaryl" as used herein means a carbonylamino group, as defined above, which has an alkylaryl group, as defined above, attached thereto.

The term "carboxy" as used herein means a

group.

The term "composition" as used herein means a product which results from the combining of more than one element or ingredient.

The phrase "EC$_{50}$ concentration" as used herein means that concentration of a compound or drug which is necessary to elicit a 50% maximal biological response and, thus, which is necessary to elicit a 50% reduction in the contractions of guinea pig ileum segments in a prostaglandin antagonism assay.

The phrase "ED$_{50}$ dose" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The abbreviation "EtOAc" as used herein means ethyl acetate.

The abbreviation "EtOH" as used herein means ethanol (CH$_3$CH$_2$OH).

The abbreviation "Et$_3$N" as used herein means triethylamine.

The abbreviation "FAB" as used herein means Fast Atom Bombardment Mass Spectroscopy.

The term "halo" or "halogen" as used herein means chlorine (Cl), bromine (Br), fluorine (F) and/or iodine (I).

The term "heteroatom" as used herein means an atom of any element other than carbon or hydrogen, such as oxygen, nitrogen or sulfur.

The abbreviation "$^1$H NMR" as used herein means Proton Nuclear Magnetic Resonance.

The abbreviation "HPLC" as used herein means High Pressure Liquid Chromatography.

The abbreviation "HRMS" as used herein means High Resolution Mass Spectroscopy.

The term "hydroxy" as used herein means the group —OH.

The term "intragastrically" and/or the abbreviation "i.g." as used herein means that a compound or drug was administered into the stomach.

The abbreviation "i.p." as used herein means that a compound or drug was administered intraperitoneally.

The abbreviation "IR" as used herein means infrared, referring to an infrared spectrum.

The abbreviation "LAH" as used herein means lithium aluminum hydride.

The abbreviation "Me" as used herein means methyl (—CH$_3$).

The abbreviation "m/e" as used herein means Mass Charge Ratio (the molecular mass divided by the charge on an election).

The abbreviation "MeOH" as used herein means methanol (CH$_3$OH).

The abbreviation "M+H" as used herein means Protonated Molecular Ion (the molecular mass of a molecule or atom plus the molecular mass of a proton).

The abbreviation "mp" as used herein means melting point.

The abbreviation "MPLC" as used herein means Medium Pressure Liquid Chromatography.

The abbreviation "MS" as used herein means Mass Spectroscopy.

The term "nitro" as used herein means an —NO$_2$ group.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D- aminoacyl residue, which may itself be N-protected similarly.

The abbreviation "RaNi" as used herein means Raney nickel.

The abbreviation "s.c." as used herein means that a compound or drug was administered subcutaneously.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

The term "trifluoromethyl" as used herein means a —$CF_3$ group.

(2) Description of Invention

In one aspect, the present invention provides compounds comprising a structure of Formula I, as described above, and pharmaceutically-acceptable salts thereof.

The compounds of the present invention comprise a class of aryl substituted dibenzoxazepine compounds in which the 2-, 3-, 5-, 7-, 8- and/or 10-position is substituted.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, regioisomers (positional isomers), such as sec-butyl, iso-butyl, 2-pyridyl, 3-pyridyl, 4-pyridyl, ortho-substituted aryl, meta-substituted aryl and the like, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. For example, Examples 19–26 hereinbelow each disclose regioisomeric mixtures of two compounds.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," J Pharm Sci 66 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine, tetra-methyl ammonium hydroxide and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are the compounds described in Example 8, Compounds E and F, Example 9, Example 16, Example 18, Example 20, Example 22, Example 30, Example 35 and Example 36. The most preferred embodiment of the invention is the compound described in Example 8, Compound E, below.

(3) Utility

Compounds of the present invention exhibit activity as prostaglandin $E_2$ antagonists (prostaglandin antagonists of the E$_2$ series) and, as such, would be useful in treating prostaglandin-E$_2$ mediated diseases.

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In General Reaction Scheme No. 1, a substituted or unsubstituted dibenzoxazepine (in which X is hydrogen, halogen or —CF$_3$, Y is hydrogen or halogen and Z is oxygen or sulfur) is reacted with a halogen substituted aromatic or heteroaromatic sulfonic or carboxylic acid chloride in the presence of a base. The resulting amide (Compound A) on heating with a secondary or primary amine under carbon monoxide atmosphere in the presence of a catalytic amount of bistriphenylphosphinepalladiumdichloride provides the desired compounds of the present invention.

Also, a substituted or unsubstituted dibenzoxazepine (in which X is hydrogen, halogen or —CF$_3$, Y is hydrogen or halogen and Z is oxygen or sulfur) may be treated with one equivalent of butyl lithium followed by a halogen substituted aromatic or heteroaromatic methyl halide to cause displacement of halogen on the methyl group to give N-substituted dibenzoxazepine. The later material on heating with a secondary or primary amine under carbonmonoxide atmosphere in the presence of a catalytic amount of bistriphenylphosphinepalladiumdichloride provides the target compounds of the present invention.

In General Reaction Scheme No. 1, R is

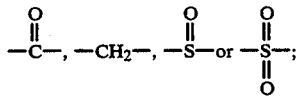

Ar is aryl; and R$^1$ is hydrogen, halogen, aryl, alkylaryl, alkenylaryl, alkynylaryl, carboxy, carbonylalkoxy or carbonylaminoalkylaryl.

In General Reaction Scheme No. 1, where Z=S, oxidation of the sulfur atom is achieved with hydrogen peroxide to produce Z as being

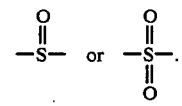

In General Reaction Scheme No. 2, Compound-A from General Reaction Scheme No. 1 is heated to 100° C. with a monosubstituted acetylene in the presence of a catalytic amount of bistriphenylphosphinepalladiumdichloride to provide compounds containing triple bonds. The triple bonds in these compounds can be reduced to a double bond or a single bond using Raney-Nickel and hydrogen. In General Reaction Scheme No. 2, X, Y, Z, R and Ar are as they are defined for General Reaction Scheme No. 1, and W is a heteroatom.

In General Reaction Scheme No. 3, a substituted or unsubstituted dibenzoxazepine is heated with an aromatic 1,2-dicarboxylic anhydride to provide an acid of this invention. (This reaction may provide a regioisomeric mixture of products which need not be separated, but can be used as such in subsequent reactions and biological testing.) The product acids can be reacted with isobutylchloroformate and 4-methylmorpholine before being treated with an alcohol or amine to provide the esters or amides of the present invention. Alternatively, especially in cases where the carboxyl functions are not in a 1,2 relationship, the bis acid chloride can be used to first acylate the dibenzoxazepine and the product reacted with an alcohol, amine or water in the presence of a base to provide the acids, alcohols or amides of this invention.

In General Reaction Scheme No. 3, X, Y and Z are as described for General Reaction Scheme No. 1 and A, B, C and D represent —CH or a heteroatom (an atom of any element other than carbon or hydrogen, such as oxygen, nitrogen or sulfur) or, in the case of a 5-membered ring, one of A, B, C or D is absent.

In all of the general reaction schemes, the aryl group represented by Ar, and any and all aryl groups included within the R$^1$ variable, may be a 5- or 6membered single-ring aromatic radical which may include 0, 1, 2, 3 or 4 heteroatoms.

GENERAL REACTION SCHEME NO. 1

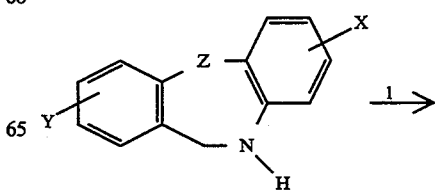

GENERAL REACTION SCHEME NO. 1 -continued

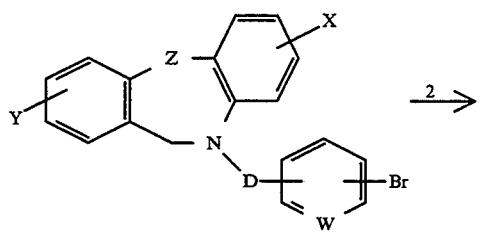

Compound - A
D = —SO$_2$, —CO or —CH$_2$
W = N or —CH—

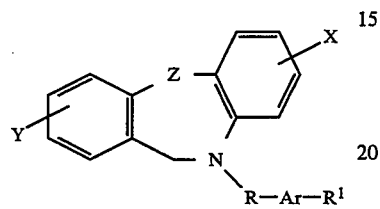

Key
1. For D = SO$_2$ or CO, the tricyclic amine is treated with bromo-substituted aromatic or heteroaromatic acid chloride (sulphonic acid chloride or carboxylic acid chloride) in the presence of triethylamine; for D = CH$_2$, the tricyclic amine is treated with n-butyl lithium (1 equivalent) before bromosubstituted aromatic or heteroaromatic methyl halide.
2. Catalytic bistriphenylphosphinepalladiumdichloride, carbonmonoxide and the amine (HN—R—Ar—R$^1$), heated at 100° C.

GENERAL REACTION SCHEME NO. 3

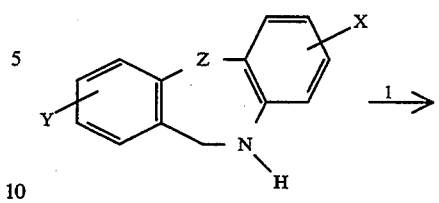

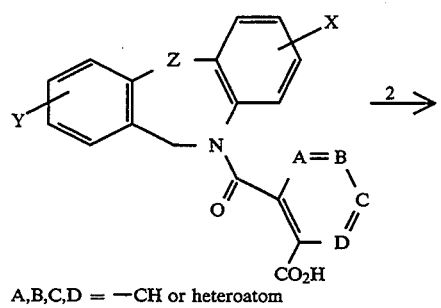

A,B,C,D = —CH or heteroatom

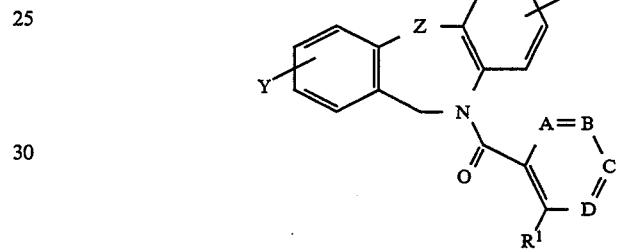

GENERAL REACTION SCHEME NO. 2

Compound A

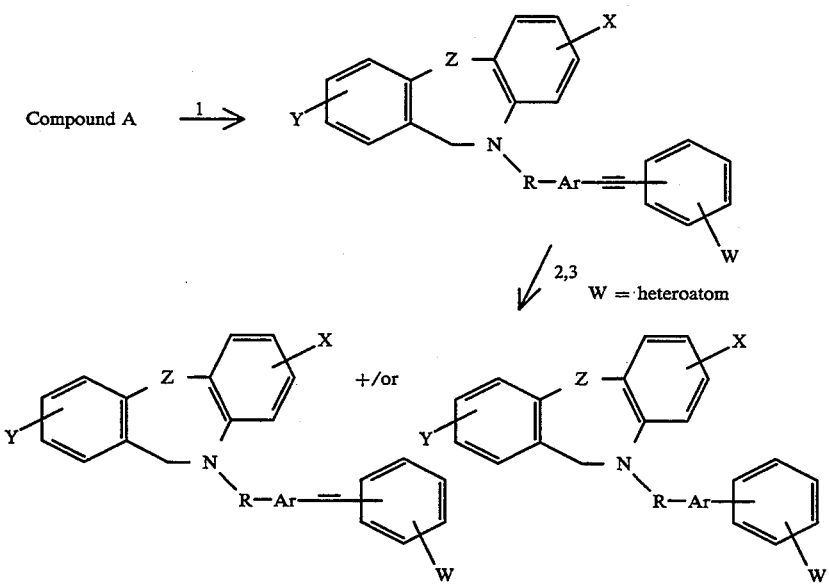

W = heteroatom

Key
1. Catalytic bistriphenylphosphinepalladiumchloride, carbonmonoxide and ethynylpyridine heat at 100° C.
2. Raney-Nickel 5 atmosphere pressure H$_2$.
3. Separate by chromatography

-continued
GENERAL REACTION SCHEME NO. 3

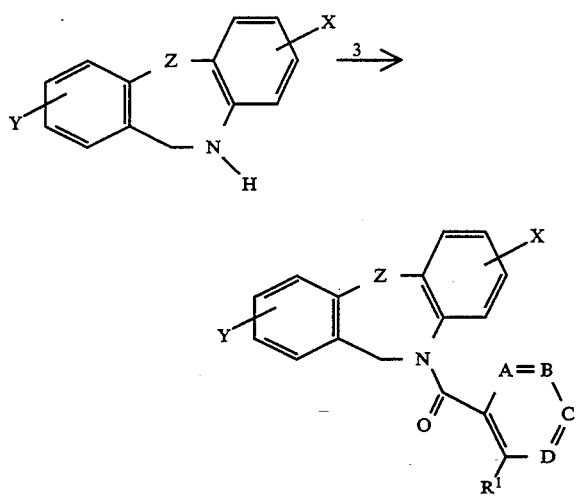

Key
1. Aromatic or heteroaromatic 1,2-dicarboxylic anhydride.
2. Isobutylchloroformate, 4-methylmorpholine, THF or CH$_2$Cl$_2$ and then amine or alcohol.
3. Aromatic or heteroaromatic dicarboxylic acid chloride and then the amine or alcohol in the presence of triethylamine.

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the salt thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All patents and publications referred to in the examples, and throughout the specification, are hereby incorporated herein by reference, without admission that such is prior art.

EXAMPLE 1

10-[(4-bromophenyl)sulfonyl]-8-chloro-10,11-dihydrodibenz[b,f][1,4]oxazepine

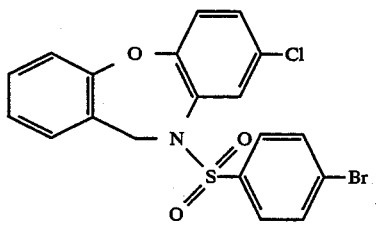

8-chloro-10,11-dihydrodibenz[b,f][1,4]oxazepine is synthesized in the manner described in U.S. Pat. No. 3,534,019, which is incorporated herein by reference.

Briefly, 200 parts of 2,5-dichloro-nitrobenzene were heated to 160° C. and stirred, and 160 parts of the potassium salt of salicylaldehyde was added over a period of 30 minutes. After the addition was complete, an exothermic reaction took place, and the temperature rose to about 195° C. Heating was discontinued until the reaction subsided, and the mixture was heated for 1 hour at 150° C. The mixture was cooled, ice and water were added, and it was extracted with ether. The ether layer was filtered to remove insoluble material, and the resultant solution was dried over sodium sulfate. The ether solvent was evaporated, and the residual oil was recrystallized from a mixture of hexane and benzene to give 2-(2-nitro-4-chloro-phenoxy)benzaldehyde melting at about 100°–101° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration, and the ethanol solvent was evaporated. The residue was dissolved in 500 parts by volume of hexane, filtered, and cooled. There was obtained yellowish-white crystals which were separated by filtration to give 8-chloro-10,11-dihydrodibenz[b,f][1,4]oxazepine melting at about 94°–95° C.

To a stirred solution of 8-chloro-10,11-dihydrodibenz[b,f][1,4]oxazepine (2 g) in chloroform (CHCl$_3$, 30 mL) was added diisopropylethylamine (1.6 mL), 4-dimethylamino-pyridine (0.02 g) and 4-bromobenzenesulphonyl chloride (2.21 g). The mixture was concentrated after 3 days and the residue was chromatographed over silica gel using 20% ethyl acetate in hexane. Appropriate fractions were pooled and concentrated to give the title compound as a white solid.

EXAMPLE 2

8-chloro-10,11-dihydro-10-[[4-[(4-pyridinyl)ethynyl]-phenyl]sulfonyl]dibenz[b,f][1,4]-oxazepine

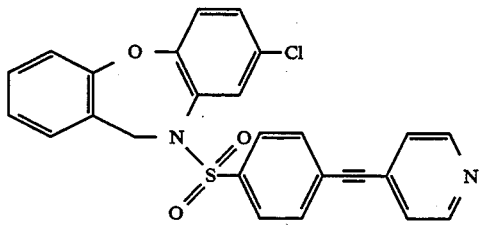

A mixture of the title product of Example 1 (0.451 g), 4-ethynylpyridine (0,116 g), bistriphenylphosphinepalladiumdichloride (0,006 g) and triethylamine (3 mL) was stirred and heated to 90° C. under a carbonmonoxide atmosphere for 2.5 hours. The mixture was cooled and chromatographed over silica gel using 40% ethyl acetate in hexane as eluant. Appropriate fractions were pooled and concentrated to give the title compound (0.42 g) as a white solid.

EXAMPLE 3

8-chloro-10,11-dihydro-10-[[[4-[2-(4-pyridinyl)ethyl]-phenyl]sulfonyl]dibenz[b,f][1,4]-oxazepine, monohydrochloride

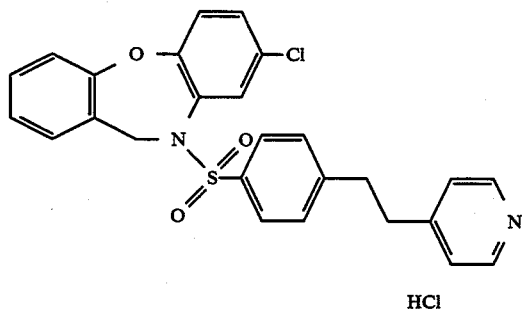

The product of Example 2 (0.35 g) was shaken in a parr hydrogenator with 5% Pd on charcoal (0.035 g) in THF (20 mL) under 5 psi of hydrogen atmosphere for 2.5 hours. The catalyst was filtered off and the filtrate was concentrated. The residue was chromatographed over silicagel using 60% ethyl acetate in hexane. Appropriate fractions were pooled and concentrated to give the free base of the title compound (0.32 g) as a white solid. The HCl salt of the free base was made as described directly below to give a white solid.

The hydrochloride salt of the free base was made either by Method-A or Method-B.

Method-A: To a solution of the free base (0.4 g) in chloroform (3 mL) was added a solution of hydrogen chloride in dioxane (7N, 1 mL). The volatiles were removed in vacuo and the residue was dried at 78° C. in vacuo (1 mm Hg) to give the title compound as a white solid.

Method-B: The free base was dissolved in a minimum amount of ethanol and excess aqueous 1 N HCl was added. The resulting solution was freeze-dried. The residue was further dried in vacuo (1 mm Hg) at 78° C. Elemental Analysis data for $C_{26}H_{21}ClN_2O_3S$. 1.3 HCl:

| Calculated | | Found |
|---|---|---|
| 60.82 | C | 60.72 |
| 4.32 | H | 4.16 |
| 5.46 | N | 5.36 |
| 13.81 | Cl | 13.34 |
| 6.24 | S | 6.19 |

EXAMPLE 4

4-[(8-chlorodibenz[b,f][1,4]oxazepin-10(11H)-yl)sulfonyl]-N-(4-pyridinylmethyl)benzamide, monohydrochloride

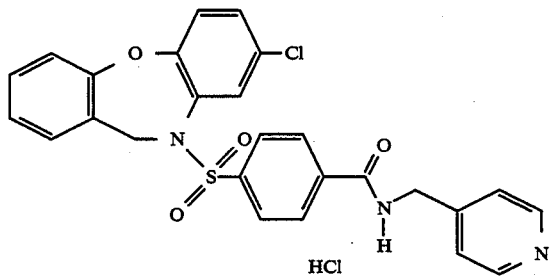

A mixture of the title product of Example 1 (0.3 g), 4-(aminomethyl)pyridine (0.3 mL), bistriphenylphosphinepalladiumdichloride (0.009 g) and tributylamine (1 mL) was stirred and heated to 100° C under a carbonmonoxide atmosphere for 4 hours and then at 60° C. for 15 hours. The mixture was cooled and chromatographed over silica gel using 2% methanol in ethyl acetate as eluant. Appropriate fractions were pooled and concentrated to give the free base of the title compound (0.38 g) as a white solid. The HCl salt of the free base was made as described in Example 3 to give a white solid.

Elemental Analysis data for $C_{26}H_{20}ClN_3O_4S$. HCl. $H_2O$:

| Calculated | | Found |
|---|---|---|
| 55.72 | C | 55.75 |
| 4.14 | H | 3.97 |
| 7.50 | N | 7.36 |
| 12.65 | Cl | 12.53 |
| 5.72 | S | 5.75 |

EXAMPLE 5

4-[(8-chlorodibenz[b,f][1,4]oxazepin-10(11H)-yl)sulfonyl]-N-(3-pyridinylmethyl)benzamide, monohydrochloride

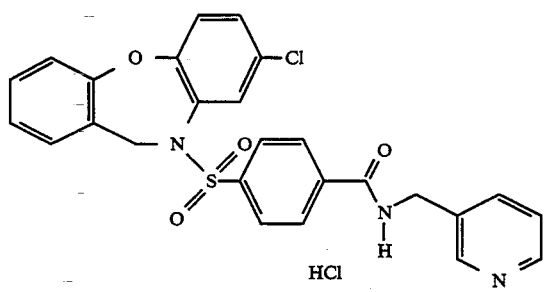

The procedure of Example 4 was repeated using 3-(aminomethyl)pyridine in the place of 4-(aminomethyl)pyridine to obtain the title compound as a white solid.

Elemental Analysis data for $C_{26}H_{20}ClN_3O_4S$. HCl. $H_2O$:

| Calculated | | Found |
|---|---|---|
| 55.72 | C | 55.86 |
| 4.14 | H | 3.90 |
| 7.50 | N | 7.47 |
| 12.65 | Cl | 12.46 |
| 5.72 | S | 5.86 |

EXAMPLE 6

10-(4-bromobenzoyl)-8-chloro-10,11-dihydrodibenz[b,f][1,4]oxazepine

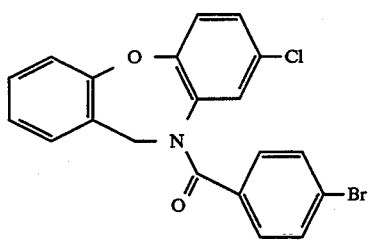

The procedure of Example 1 was repeated using 4-bromobenzoylchloride in the place of 4-bromobenzenesulphonyl chloride to obtain the title compound as a white solid.

EXAMPLE 7

8-chloro-10,11-dihydro-10-[4-[(4-pyridinyl)ethynyl]-benzoyl]dibenz[b,f][1,4]oxazepine

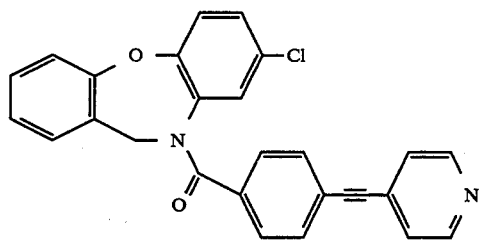

The procedure of Example 2 was repeated using the title product of Example 5 in the place of the title product of Example 1 to obtain the title compound as a white solid.

EXAMPLE 8

Compound E 8-chloro-10,11-dihydro-10-[4-[2Z-(4-pyridinyl)ethenyl]benzoyl]dibenz[b,f][1,4]oxazepine, hydrochloride

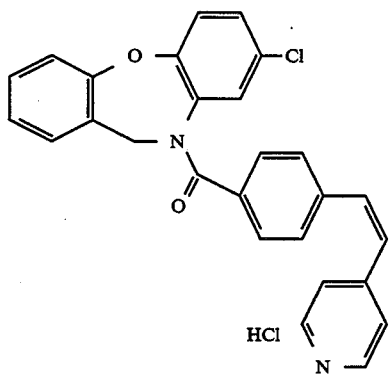

Compound F 8-chloro-10,11-dihydro-10-[4-[2-(4-pyridinyl)ethyl]benzoyl]dibenz[b,f][1,4]oxazepine, hydrochloride

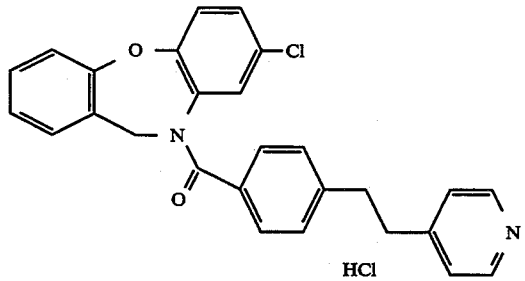

The product of Example 7 (0.47 g) was shaken in a parr hydrogenator with Raney-Nickel (0.5 g) in methanol (20 mL) under 5 psi of hydrogen atmosphere for 4 hours. The catalyst was filtered off and the filtrate was concentrated. The residue was chromatographed using ethyl acetate in hexane as eluant. Appropriate fractions were pooled and concentrated to give Compound E (less polar, 0.28 g) and Compound F (more polar, 0.19 g), the free bases of the title compounds as white solids.

The HCl salts of the free bases were made as described in Example 3.

Compound E

Elemental Analysis data for $C_{27}H_{19}ClN_2O_2 \cdot 1.25$ HCl $\cdot 1.25$ $H_2O$:

| Calculated | | Found |
|---|---|---|
| 63.96 | C | 63.83 |
| 4.52 | H | 4.18 |
| 5.53 | N | 5.42 |
| 15.73 | Cl | 15.93 |

Compound F

Elemental Analysis data for $C_{27}H_{21}ClN_2O_2 \cdot 1.25$ HCl $\cdot 1.25$ $H_2O$:

| Calculated | | Found |
|---|---|---|
| 63.71 | C | 63.70 |
| 4.90 | H | 4.57 |
| 5.50 | N | 5.40 |
| 15.67 | Cl | 15.13 |

EXAMPLE 9

4-[(8-chlorodibenz[b,f][1,4]oxazepin-10(11H)-yl)carbonyl]-N-(4-pyridinylmethyl)benzamide hydrochloride

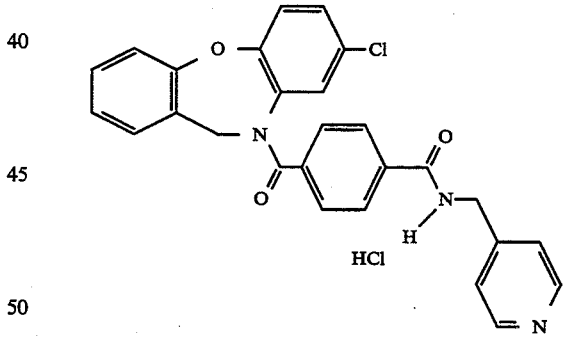

The procedure of Example 4 was repeated using the title product of Example 6 in the place of the title product of Example 1 to obtain the title compound as a white solid.

Elemental Analysis data for $C_{27}H_{20}ClN_3O_3 \cdot 0.9$ HCl $\cdot 1.5$ $H_2O$:

| Calculated | | Found |
|---|---|---|
| 61.22 | C | 61.40 |
| 4.55 | H | 4.20 |
| 7.93 | N | 7.89 |
| 12.72 | Cl | 12.76 |

EXAMPLE 10

4-[(8-chlorodibenz[b,f][1,4]oxazepin-10(11H)-yl)carbonyl]-N-(3-pyridinylmethyl)benzamide, hydrochloride

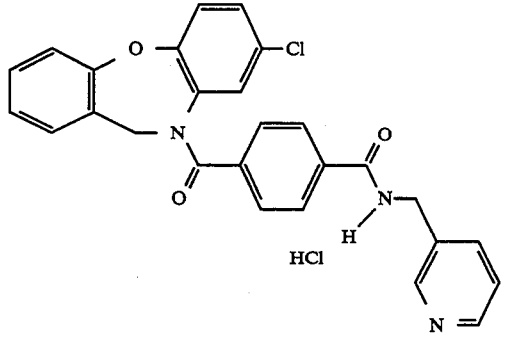

The procedure of Example 9 was repeated using 3-aminomethylpyridine in the place of 4-aminomethylpyridine to obtain the title compound as a white solid. Elemental Analysis data for $C_{27}H_{20}ClN_3O_3S \cdot 0.9$ HCl $\cdot 2$ $H_2O$:

| Calculated | | Found |
|---|---|---|
| 60.19 | C | 60.51 |
| 4.66 | H | 4.06 |
| 7.80 | N | 7.78 |
| 12.50 | Cl | 12.33 |

EXAMPLE 11

2-[(8-chlorodibenz[b,f][1,4]oxazepin-10(11H)-yl)carbonyl]benzoic acid

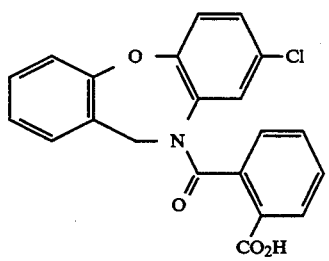

A stirred mixture of 8-chloro-dibenz[b,f]-[1,4]oxazepine (3.35 g) and phthalic anhydride (2.13 g) in THF (40 mL) was heated to reflux for 4 days. The mixture was concentrated and the residue was triturated with ether. The precipitated solid was filtered to give the title compound as a white solid (3.84 g).

EXAMPLE 12

2-[(8-chlorodibenz[b,f][1,4]oxazepin-10(11H)-yl)carbonyl]-N-(4-pyridinylmethyl)benzamide, hydrochloride

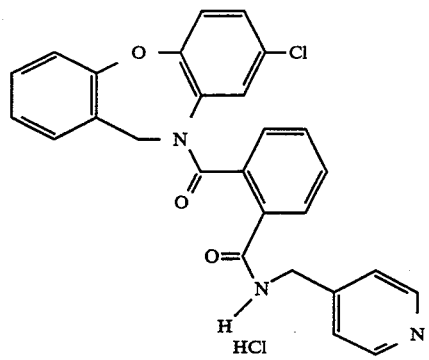

To a stirred solution of the title product of Example 11 (0.55 g) in $CH_2Cl_2$ (10 mL) at 0° C. was added 1-methyl morpholine (0.168 mL) and isobutylchloroformate (0.199 mL) successively. After 30 minutes, 4-(aminomethyl)pyridine (0.156 mL) was added. The mixture was allowed to warm to ambient temperature for hours. The mixture was extracted with ethyl acetate and water. The organic extract was dried over MgSO4 and concentrated. The residue was purified by chromatography over silica gel using ethyl acetate as eluant to give the free base of the title compound as a white solid. The hydrochloride salt of the free base was made in the manner described in Example 3 to give the title compound.

Elemental Analysis data for $C_{27}H_{20}ClN_3O_3 \cdot 1.3$ HCl $\cdot 1$ $H_2O$:

| Calculated | | Found |
|---|---|---|
| 60.58 | C | 60.40 |
| 4.39 | H | 4.49 |
| 7.85 | N | 7.64 |
| 15.23 | C | 15.61 |

EXAMPLE 13

2-(8-chlorodibenz[b,f][1,4]oxazepin-10(11H)-yl)carbonyl]-N-(3-pyridinylmethyl)benzamide hydrochloride

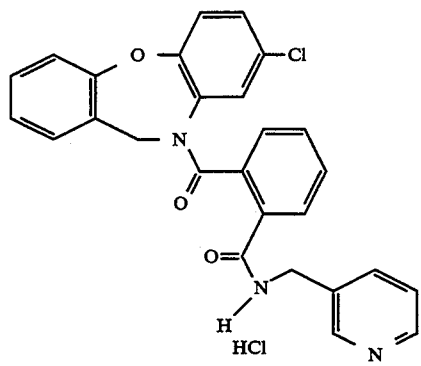

The procedure of Example 12 was repeated using 3-(aminomethyl)pyridine in the place of 4-(aminomethyl)pyridine to obtain the title compound as a white solid.

Elemental Analysis data for $C_{27}H_{20}ClN_3O_3$. 1.3 HCl. 1 $H_2O$:

| Calculated | | Found |
|---|---|---|
| 60.58 | C | 60.47 |
| 4.39 | H | 4.63 |
| 7.85 | N | 7.54 |
| 15.23 | C | 15.42 |

EXAMPLE 14

2-[(8-chlorodibenz[b,f][1,4]oxazepin-10(11H)-yl]carbonyl-]-N-(2-pyridinylmethyl)benzamide, dihydrochloride

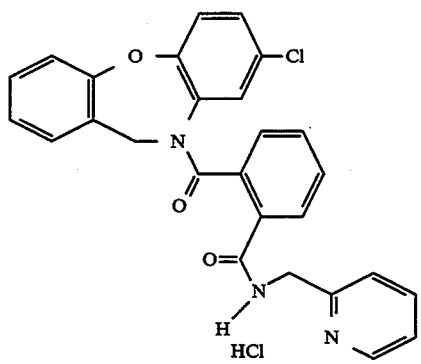

The procedure of Example 12 was repeated using 2-(aminomethyl)pyridine in the place of 4-(aminomethyl)pyridine to obtain the title compound as a white solid.

Elemental Analysis data for $C_{27}H_{20}ClN_3O_3$. 2 HCl 1.8 $H_2O$:

| Calculated | | Found |
|---|---|---|
| 56.37 | C | 56.67 |
| 4.69 | H | 4.28 |
| 7.30 | N | 7.12 |
| 18.49 | Cl | 18.15 |

EXAMPLE 15

10-(3-bromobenzoyl)-8-chloro-10,11-dihydrodibenz[b,f][1,4]oxazepine

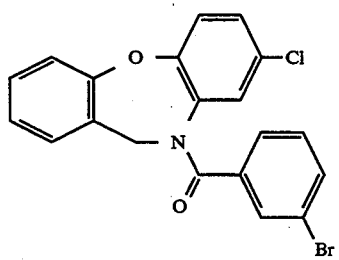

The procedure of Example 1 was repeated using 3-bromobenzoylchloride in the place of 4-bromobenzenesulphonyl chloride to obtain the title compound as a white solid.

EXAMPLE 16

3-[(8-chlorodibenz[b,f][1,4]oxazepin-10(11H)-yl)carbonyl]-N-(4-pyridinylmethyl)benzamide, monohydrochloride

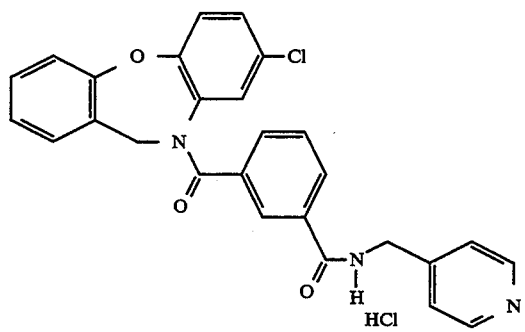

The procedure of Example 4 was repeated using the product of Example 15 in the place of the product of Example 1 (and conducting the reaction at 100° C. for 16 hours) to obtain the title compound as a white solid.

Elemental Analysis data for $C_{27}H_{20}ClN_3O_3$. 1 HCl. 1.25 $H_2O$:

| Calculated | | Found |
|---|---|---|
| 61.31 | C | 61.19 |
| 4.48 | H | 4.75 |
| 7.94 | N | 7.59 |
| 13.41 | Cl | 13.58 |

EXAMPLE 17

3-[(8-chlorodibenz[b,f][1,4]oxazepin-10(11H)-yl)carbonyl]-N-(3-pyridinylmethyl)benzamide, monohydrochloride

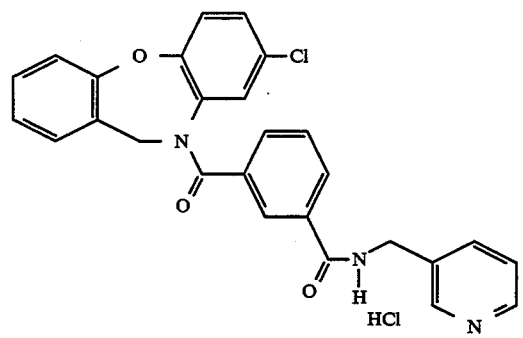

The procedure of Example 16 was repeated using 3-(aminomethyl)pyridine in the place of 4-(aminomethyl)pyridine to obtain the title compound as a white solid.

Elemental Analysis data for $C_{27}H_{20}ClN_3O_3$. 1 HCl.3.5 $H_2O$:

| Calculated | | Found |
|---|---|---|
| 56.95 | C | 56.42 |
| 4.96 | H | 4.31 |
| 7.38 | N | 7.09 |

| Calculated | | Found |
|---|---|---|
| 12.45 | Cl | 12.94 |

EXAMPLE 18

3-[(8-chlorodibenz[b,f][1,4]oxazepin-10(11H)-yl)carbonyl]-N-(2-pyridinylmethyl)benzamide, hydrochloride

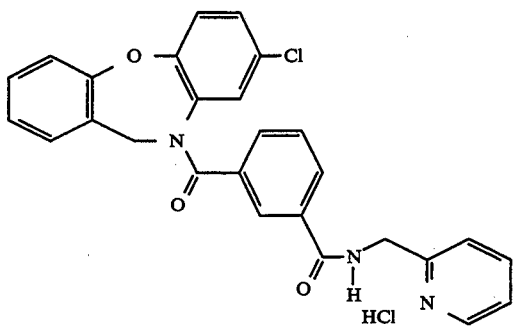

The procedure of Example 17 was repeated using 2-(aminomethyl)pyridine in the place of 4-(aminomethyl)pyridine to obtain the title compound as a white solid.

Elemental Analysis data for $C_{27}H_{20}ClN_3O_3 \cdot 1.25$ HCl $\cdot$ 1.5 $H_2O$:

| Calculated | | Found |
|---|---|---|
| 59.78 | C | 59.53 |
| 4.51 | H | 4.47 |
| 7.75 | N | 7.56 |
| 14.70 | Cl | 14.49 |

EXAMPLE 19

Compound G

2-[(8-chlorodibenz[b,f][1,4]oxazepin-10(11H)-yl)carbonyl]amino]-3-pyridinecarboxylic acid

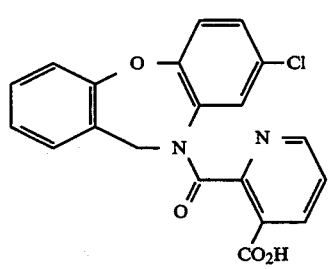

Compound H

3-[(8-chlorodibenz[b,f][1,4]oxazepin-10(11H)-yl)carbonyl]-2-pyridinecarboxylic acid

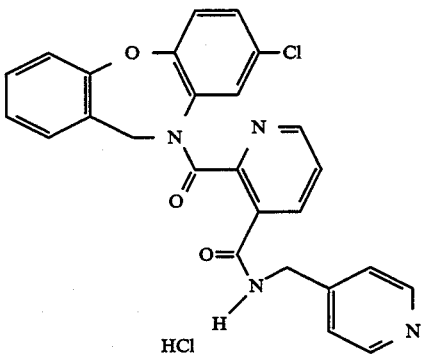

The procedure of Example 11 was repeated using pyridine-2,3-dicarboxylic anhydride in the place of phthalic anhydride to obtain a 3:1 mixture of Compound G and Compound H as a white solid. The mixture was used as such in the subsequent examples.

Elemental Analysis data for $C_{20}H_{13}ClN_2O_4 \cdot 0.5$ $H_2O$:

| Calculated | | Found |
|---|---|---|
| 61.63 | C | 61.72 |
| 3.62 | H | 3.86 |
| 7.19 | N | 6.95 |
| 9.10 | Cl | 8.86 |

EXAMPLE 20

Compound I

2-[(8-chlorodibenz[b,f][1,4]oxazepin-10(11H)-yl)carbonyl]-N-(4-pyridinylmethyl)-3-pyridinecarboxamide, dihydrochloride

Compound J

3[(8-chlorodibenz[b,f][1,4]oxazepin-10(11H)-yl)carbonyl]-N-(4-pyridinylmethyl)-2-pyridinecarboxamide, monohydrochloride

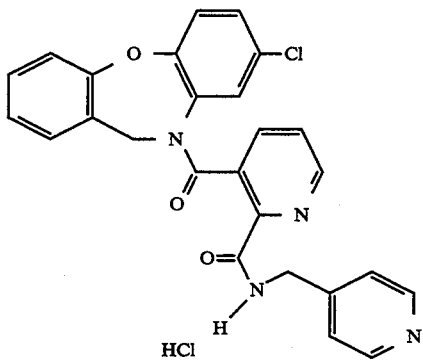

The procedure of Example 12 was repeated using the product of Example 19 in the place of the product of Example 11. A solution of the crude product in a small amount of CH$_2$Cl$_2$ was triturated with excess ether and the precipitated solid was filtered to obtain a 3:1 mixture of Compound I and Compound J as a white solid. The HCl salts of the free bases were made as described in Example 3.

Elemental Analysis data for C$_{26}$H$_{19}$ClN$_4$O$_3$. 2 HCl. 1.5 H$_2$O:

| Calculated | | Found |
|---|---|---|
| 54.70 | C | 54.88 |
| 4.20 | H | 3.99 |
| 9.81 | N | 9.87 |
| 18.63 | Cl | 18.77 |

EXAMPLE 21

Compound K

2-[(8-chlorodibenz[b,f][1,4]oxazepin-10(11H)-yl)carbonyl]-N-(3-pyridinylmethyl)-3-pyridinecarboxamide, dihydrochloride

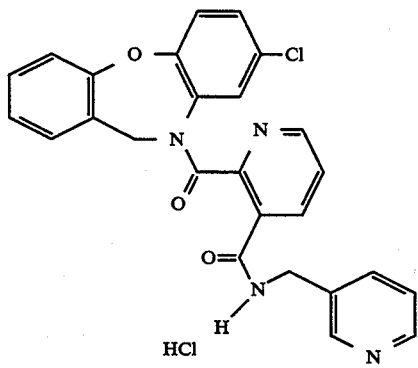

Compound L

3-[(8-chlorodibenz[b,f][1,4-oxazepin-10(11H)-yl)carbonyl]-N-(3-pyridinylmethyl)-2-pyridinecarboxamide

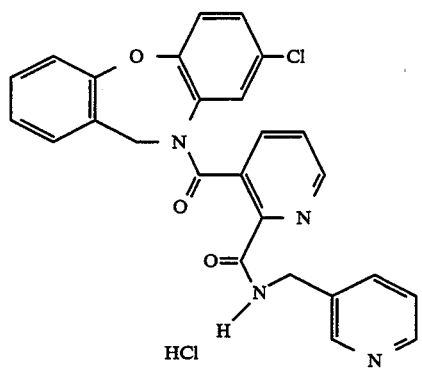

The procedure of Example 20 was repeated using 3(aminomethyl)pyridine in the place of 4-(aminomethyl)pyridine to obtain a 3:1 mixture of Compound K and Compound L as a white solid.

Elemental Analysis data for C$_{26}$H$_{19}$ClN$_4$O$_3$. 2 HCl. 1 H$_2$O:

| Calculated | | Found |
|---|---|---|
| 55.58 | C | 55.14 |
| 4.13 | H | 4.02 |
| 9.97 | N | 9.95 |
| 18.93 | Cl | 19.12 |

EXAMPLE 22

Compound M

2-[(8-chlorodibenz[b,f][1,4]oxazepin-10(11H)-yl)carbonyl]-N-(2-pyridinylmethyl)-3-pyridinecarboxamide, dihydrochloride

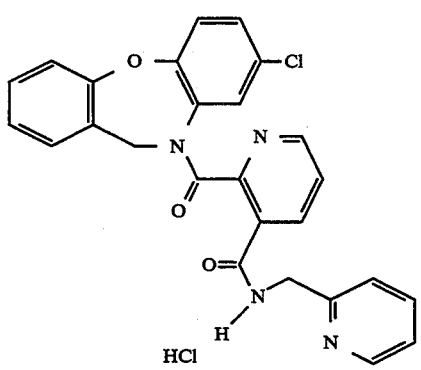

Compound N

3-[(8-chlorodibenz[b,f][1,4]oxazepin-10(11H)-yl)car-
bonyl]-N-(2-pyridinylmethyl)-2-pyridinecarboxamide,
monohydrochloride

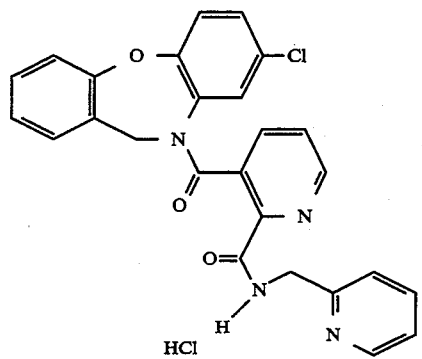

The procedure of Example 20 was repeated using
2-(aminomethyl)pyridine in the place of 4-(aminome-
thyl)pyridine to obtain a 3:1 mixture of Compound M
and Compound N as a white solid.

Elemental Analysis data for $C_{26}H_{19}ClN_4O_3 \cdot 2$ HCl $\cdot$ 2 $H_2O$:

| Calculated | | Found |
|---|---|---|
| 53.85 | C | 54.02 |
| 4.35 | H | 3.99 |
| 9.66 | N | 9.78 |
| 18.34 | Cl | 18.64 |

EXAMPLE 23

Compound O

4-[(8-chlorodibenz[b,f][1,4]oxazepin-10(11H)-yl)car-
bonyl]-3-pyridinecarboxylic acid

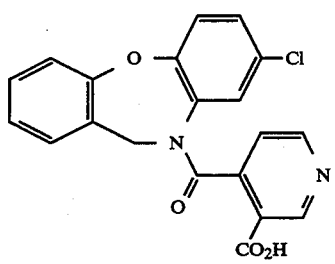

Compound P

3-[(8-chlorodibenz[b,f][1,4]oxazepin-10(11H)-yl)car-
bonyl]-4-pyridinecarboxylic acid

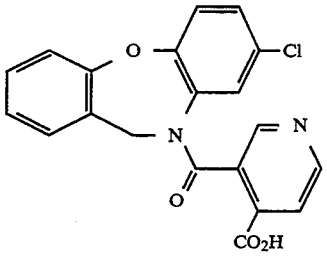

The procedure of Example 19 was repeated using
pyridine-3,4-dicarboxylic anhydride in the place of
pyridine-2,3-dicarboxylic anhydride to obtain a 3:1 mix-
ture of Compound O and Compound P as a white solid.
The mixture was used as such in the subsequent exam-
ples.

EXAMPLE 24

Compound Q

4-[(8-chlorodibenz[b,f][1,4]oxazepin-10(11H)-yl)car-
bonyl]-N-(4-pyridinylmethyl)-3-pyridinecarboxamide,
dihydrochloride

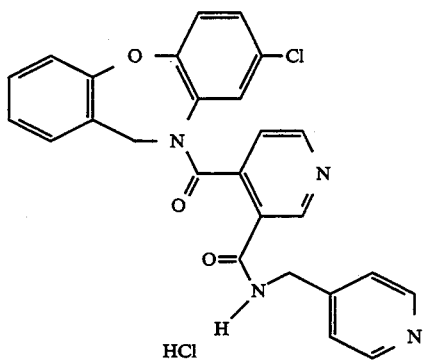

Compound R

3-[(8-chlorodibenz[b,f][1,4]oxazepin-10(11H)-yl)car-
bonyl]-N-(4-pyridinylmethyl)-4-pyridinecarboxamide,
monohydrochloride

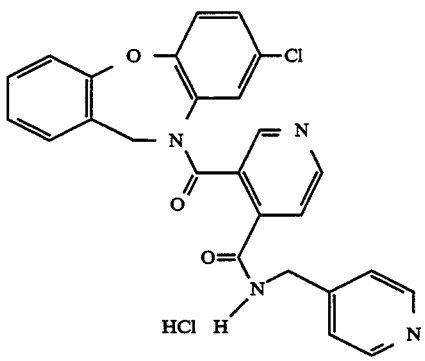

The procedure of Example 12 was repeated using the
product of Example 23 in the place of the product of Example 11 to obtain a 3:1 mixture of Compound Q and Compound R as a white solid.

Elemental Analysis data for $C_{26}H_{19}ClN_4O_3 \cdot 2\,HCl \cdot 1.5\,H_2O$:

| Calculated | | Found |
|---|---|---|
| 53.85 | C | 54.43 |
| 4.35 | H | 3.97 |
| 9.66 | N | 9.87 |
| 18.34 | Cl | 18.30 |

EXAMPLE 25

Compound S

4-[(8-chlorodibenz[b,f][1,4]oxazepin-10(11H)-yl)carbonyl]-N-(3-pyridinylmethyl)-3-pyridinecarboxamide, hydrochloride

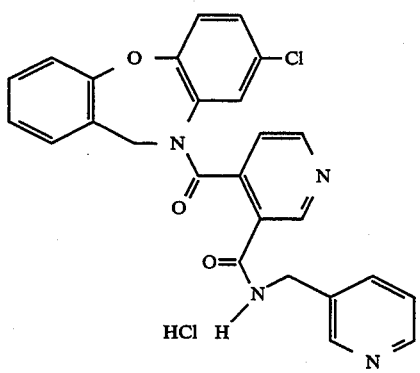

Compound T

3-[(8-chlorodibenz[b,f][1,4]oxazepin-10(11H)-yl)carbonyl]-N(3-pyridinylmethyl)-4-pyridinecarboxamide, monohydrochloride

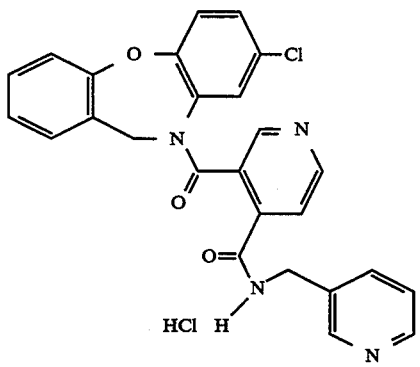

The procedure of Example 24 was repeated using 3-(aminomethyl)pyridine in the place of 4-(aminomethyl)pyridine to obtain a 3:1 mixture of Compound S and Compound T as a white solid.

Elemental Analysis data for $C_{26}H_{19}ClN_4O_3 \cdot 2.4\,HCl \cdot 2.1\,H_2O$:

| Calculated | | Found |
|---|---|---|
| 52.37 | C | 52.03 |
| 4.33 | H | 4.45 |
| 9.40 | N | 10.28 |

-continued

| Calculated | | Found |
|---|---|---|
| 20.22 | Cl | 19.91 |

EXAMPLE 26

Compound U

4-[(8-chlorodibenz[b,f][1,4]oxazepin-10(11H)-yl)carbonyl]-N-(3-pyridinylmethyl)-3-pyridinecarboxamide, hydrochloride

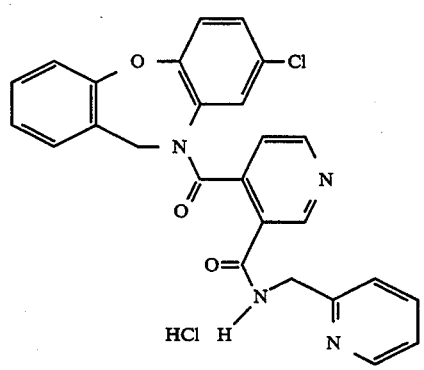

Compound V

3-[(8-chlorodibenz[b,f][1,4]oxazepin-10(11H)-yl)carbonyl]-N-(2-pyridinylmethyl)-4-pyridinecarboxamide, monohydrochloride

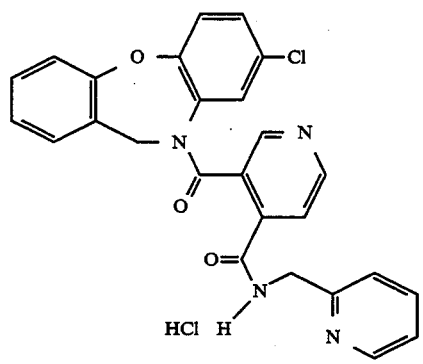

The procedure of Example 24 was repeated using 2-(aminomethyl)pyridine in the place of 4-(aminomethyl)pyridine to obtain a 3:1 mixture of Compound M and Compound N as a white solid.

Elemental Analysis data for $C_{26}H_{19}ClN_4O_3 \cdot 2.5\,HCl \cdot 3\,H_2O$:

| Calculated | | Found |
|---|---|---|
| 50.69 | C | 50.02 |
| 4.50 | H | 4.11 |
| 9.09 | N | 9.10 |
| 20.14 | Cl | 20.11 |

EXAMPLE 27

4-[(8-chlorodibenz[b,f][1,4]oxazepin-10(11H)-yl)methyl]-N-(4-pyridinylmethyl) benzamide, hydrochloride

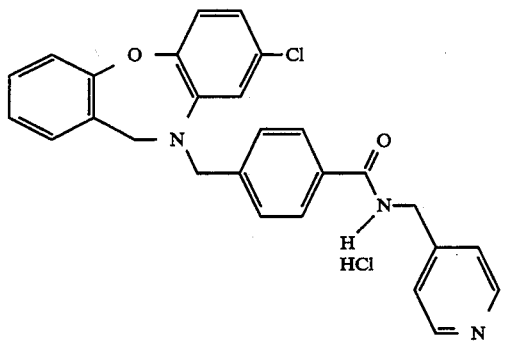

The procedure of Example 12 was repeated using 4-(8-chloro-10,11-dihydrodibenzo[b,f][1,4]oxazepin-10-ylmethyl)-benzoic acid in the place of the title product of Example 11 to obtain the title compound as a white solid.

Elemental Analysis data for $C_{27}H_{22}ClN_3O_2 \cdot 1.5$ HCl $\cdot$ 2 $H_2O$:

| Calculated | | Found |
|---|---|---|
| 59.32 | C | 59.72 |
| 5.07 | H | 5.00 |
| 7.69 | N | 7.46 |
| 16.21 | Cl | 16.51 |

EXAMPLE 28

4-[(8-chlorodibenz[b,f][1,4]oxazepin-10(11H)-yl)methyl]-N-(3-pyridinylmethyl) benzamide, hydrochloride

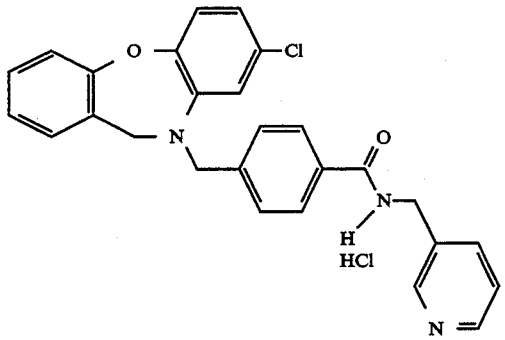

The procedure of Example 27 was repeated using 3-(aminomethyl)pyridine in the place of 4-(aminomethyl)pyridine to obtain the title compound as a white solid.

Elemental Analysis data for $C_{27}H_{22}ClN_3O_2 \cdot 1.5$ HCl $\cdot$ 1.5 $H_2O$:

| Calculated | | Found |
|---|---|---|
| 60.32 | C | 60.59 |
| 4.97 | H | 4.79 |
| 7.82 | N | 7.73 |
| 16.48 | Cl | 17.19 |

EXAMPLE 29

4-[(8-chlorodibenz[b,f][1,4]oxazepin-10(11H)-yl)methyl]-N-(2-pyridinylmethyl)benzamide, hydrochloride

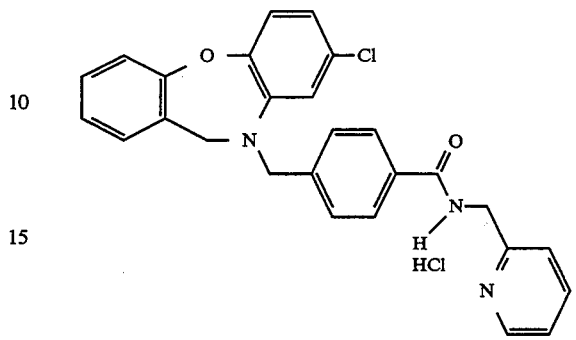

The procedure of Example 27 was repeated using 2-(aminomethyl)pyridine in the place of 4-(aminomethyl)pyridine to obtain the title compound as a white solid.

Elemental Analysis data for $C_{27}H_{22}ClN_3O_2 \cdot 1.5$ HCl $\cdot$ 1.5 $H_2O$:

| Calculated | | Found |
|---|---|---|
| 60.32 | C | 60.99 |
| 4.97 | H | 4.65 |
| 7.82 | N | 7.75 |
| 16.48 | Cl | 16.86 |

EXAMPLE 30

6-[(8-chlorodibenz[b,f][1,4]oxazepin-10(11H)-yl)carbonyl]-N-(4-pyridinylmethyl )-2-pyridinecarboxamide, hydrochloride

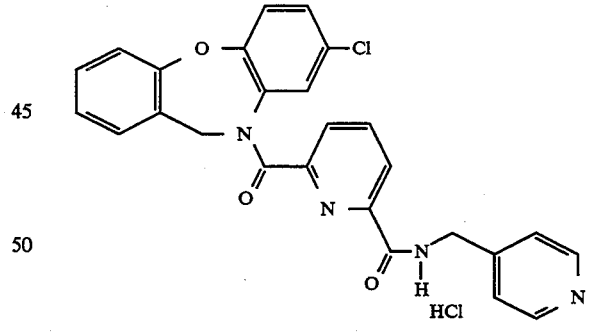

A solution of 8-chloro-dibenz[b,f][1,4]oxazepine (0.77 g), 2,6-pyridine-dicarbonyl chloride (0.68 g) and 4-methylmorpholine (0.367 mL) in CHCl$_3$ (33 mL) was allowed to stand at ambient temperature for 16 hours. To this solution was added 4-(aminomethyl)pyridine (0.34 mL) and the mixture was allowed to stand at ambient temperature for 16 hours. The mixture was concentrated and the residue was extracted with ethyl acetate and saturated NaHCO$_3$. The organic extract was concentrated and the residue chromatographed over silica gel using 50% ethyl acetate in hexane. Appropriate fractions were pooled and concentrated to give the free base of the title compound as a white solid. The HCl salt of the free base was made as described in Example 3.

Elemental Analysis data for C$_{26}$H$_{19}$ClN$_4$O$_3$. 1.25 HCl. 1.25 H$_2$O:

| Calculated | | Found |
|---|---|---|
| 57.94 | C | 57.41 |
| 4.25 | H | 4.05 |
| 10.39 | N | 10.20 |
| 14.80 | Cl | 14.43 |

EXAMPLE 31

6-[(8-chlorodibenz[b,f][1,4]oxazepin-10(11H)-yl)carbonyl]-N-(3-pyridinylmethyl)-2pyridinecarboxamide, hydrochloride

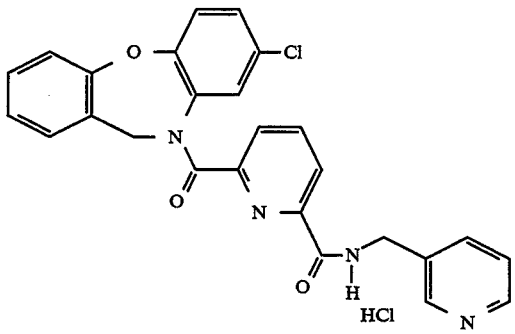

The procedure of Example 30 was repeated using 3-(aminomethyl)pyridine in the place of 4-(aminomethyl)pyridine to obtain the title compound as a white solid.

Elemental Analysis data for C$_{26}$H$_{19}$ClN$_4$O$_3$. 1.1 HCl. 1.25 H$_2$O:

| Calculated | | Found |
|---|---|---|
| 58.53 | C | 58.11 |
| 4.25 | H | 3.92 |
| 10.50 | N | 10.27 |
| 13.95 | Cl | 14.24 |

EXAMPLE 32

6-[(8-chlorodibenz[b,f][1,4]oxazepin-10(11H)-yl)carbonyl]-N-(2-pyridinylmethyl)-2-pyridinecarboxamide, hydrochloride

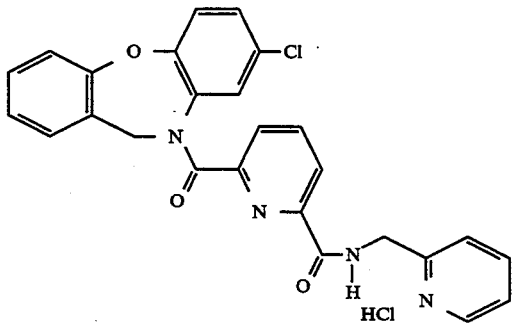

The procedure of Example 30 was repeated using 2-(aminomethyl)pyridine in the place of 4-(aminomethyl)pyridine to obtain the title compound as a white solid.

Elemental Analysis data for C$_{26}$H$_{19}$ClN$_4$O$_3$. 1.25 HCl. 2 H$_2$O:

| Calculated | | Found |
|---|---|---|
| 56.52 | C | 56.58 |
| 4.42 | H | 4.04 |
| 10.14 | N | 9.92 |
| 14.44 | Cl | 14.84 |

EXAMPLE 33

10-[(2-bromo-5-pyridinyl)methyl]-8-chloro-10,11-dihydrodibenz[b,f][1,4]oxazepine

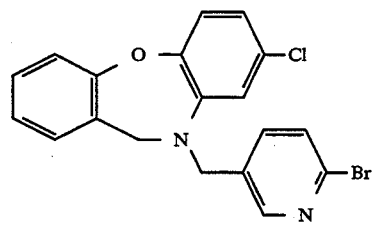

6-Hydroxynicotinic acid (31 g) and methylene bromide (300 mL) were added at 18° C. to 98.9 g of phosphorous pentabromide while stirring with a mechanical stirrer under an argon atmosphere. The mixture was warmed to 70° C. over 2 hours, and further stirred for 16 hours. The mixture was cooled to 10° C. and 300 mL of methanol (CAUTION: EXOTHERMIC) was added. The cooling bath was removed and stirring was continued for ½ hour more. A solution of 76 g of K$_2$CO$_3$ in 610 mL of water was added and stirred for a few minutes. The layers were separated. The aqueous layer was extracted with methylene bromide. The combined organic phase was filtered through celite, washed with water and stripped. The residue was dissolved in 200 mL of ethanol on the steam bath. To this hot solution, 400 mL of water was added and the mixture was cooled in an ice bath. The precipitated solid was filtered, washed with 20% ethanol in water and air-dried to give 38.3 g of methyl 6-bromo-nicotinate as a solid.

To a mechanically-stirred solution of 80 g of methyl 6-bromo-nicotinate in a mixture of 386 mL of tetrahydrofuran and 114 mL of toluene at 0° C. was added drop by drop a 1.5 molar toluene solution of diisobutyl aluminium hydride at a rate such that the temperature never exceeded 10° C. This addition took 50 minutes. 21.59 mL of methyl ethyl ketone was added to the reaction mixture while the temperature rose to 25° C. A solution of 2.58 g of NaOH in 40 mL of water was added to the reaction mixture drop by drop (CAUTION: EXOTHERMIC). 121 mL of water was added with vigorous stirring. After completion of the addition, a white solid appeared. The mixture was filtered through celite and 196 mL of toluene was used to wash the solid and filter. The filtrate was concentrated in vacuo and 48 mL of heptane was added. The mixture was cooled in an ice-salt bath for 1 hour. The precipitated solid was filtered and washed with heptane to give 62.09 g of 3-hydroxymethyl-6-bromopyridine as a solid.

To a mechanically-stirred solution of 78.12 g of thionyl chloride in 450 mL of acetonitrile at 15° C. was added a solution of 160.75 g of 3-hydroxymethyl-6-bromopyridine in 446 mL of acetonitrile over 30 minutes. The temperature rose to 22° C. during the addition, and the reaction mixture was stirred for 15 minutes at room temperature. The mixture was cooled in an ice bath, and a solution of 70 g of NaOH in 1.4 L of water was added at such a rate that the temperature did not exceed 15° C. 603 mL of toluene was added to the mixture and stirred rapidly. The layers were separated. The aqueous phase was reextracted with toluene. The combined organic phase was concentrated in vacuo to give 181.61 g of 3-chloromethyl-6-bromopyridine.

To a stirred solution of 8-chloro-10,11-dihydrodibenz[b,f][1,4]oxazepine (2 g) in THF (25 mL) at −78° C. was added 1.6 M hexane solution of n-butyl lithium (5.4 mL). After 25 minutes, 3-chloromethyl-6-bromopyridine (1.79 g) in THF (5 mL) was added. After 30 minutes, the temperature was raised to −23° C. After 30 minutes, an excess saturated solution of NH$_4$Cl was added and the mixture was extracted with ether. The organic extract was dried over MgSO$_4$ and concentrated. The residue was chromatographed over silica gel using 10% ethyl acetate in hexane as eluant. Appropriate fractions were pooled to give the title compound (2.8 g) as a thick gum.

EXAMPLE 34

5-[(8-chlorodibenz[b,f][1,4]oxazepin-10(11H)yl)methyl]-N-(4-pyridinylmethyl)-2-pyridinecarboxamide, monohydrochloride

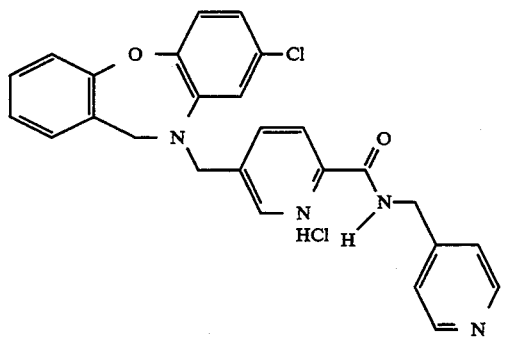

A mixture of the product of Example 33 (0,658 g), 4-(aminomethyl)pyridine (2.5 mL) and bistriphenylphosphinepalladiumdichloride (0.020 g) was heated at 100° C. under 60 psi carbonmonoxide pressure for 16 hours. The mixture was triturated with hexane (100 mL) and the supernatent discarded. The residue was chromatographed over silica gel using 4% methanol in ethyl acetate as eluant to give the free base of the title compound as a white solid. The HCl salt of the free base was made as described in Example 3 to give a white solid.

Elemental Analysis data for C$_{26}$H$_{21}$ClN$_4$O$_2$. 2 HCl. 1.5 H$_2$O:

| Calculated | | Found |
|---|---|---|
| 56.08 | C | 55.89 |
| 4.71 | H | 4.49 |
| 10.06 | N | 9.48 |
| 19.10 | Cl | 19.53 |

EXAMPLE 35

5-[(8-chlorodibenz[b,f][1,4]oxazepin-10(11H)-yl)methyl]-N-(3-pyridinylmethyl)-2-pyridinecarboxamide, monohydrochloride

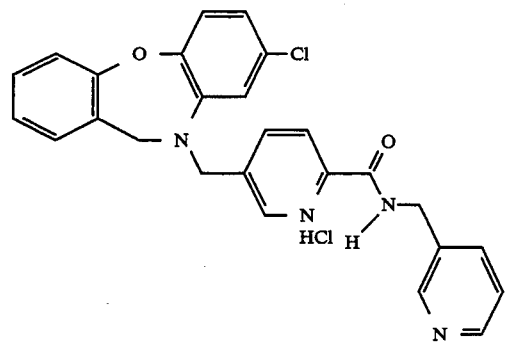

The procedure of Example 34 was repeated using 3-(aminomethyl)pyridine in the place of 4-(aminomethyl)pyridine to obtain the title compound as a white solid.

Elemental Analysis data for C$_{26}$H$_{21}$ClN$_4$O$_2$. 2.25 HCl. 1.75 H$_2$O:

| Calculated | | Found |
|---|---|---|
| 54.74 | C | 54.89 |
| 4.73 | H | 4.60 |
| 9.82 | N | 9.46 |
| 20.20 | Cl | 20.69 |

EXAMPLE 36

5-[(8-chlorodibenz[b,f][1,4]oxazepin-10(11H)-yl)methyl]-N-(2-pyridinylmethyl)-2-pyridinecarboxamide, monohydrochloride

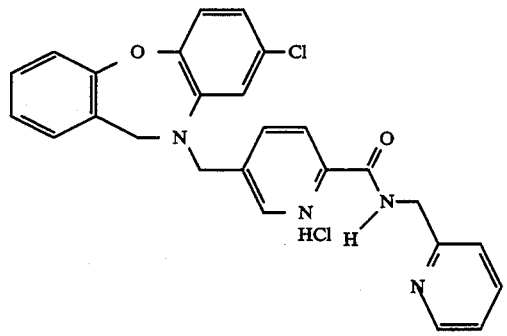

The procedure of Example 35 was repeated using 2-(aminomethyl)pyridine in the place of 4-(aminomethyl)pyridine to obtain the title compound as a white solid.

Elemental Analysis data for C$_{26}$H$_{21}$ClN$_4$O$_2$. 2.5 HCl. 2 H$_2$O:

| Calculated | | Found |
|---|---|---|
| 53.46 | C | 53.50 |
| 4.75 | H | 4.51 |
| 9.59 | N | 9.47 |
| 21.24 | Cl | 21.83 |

EXAMPLE 37

10-(Benzoyl)-8-chloro-10,11-dihydrodibenz[b,f][1,4]oxazepine

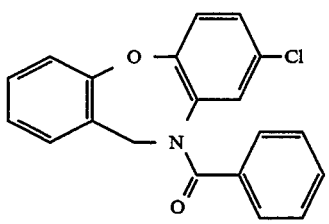

The procedure of Example 1 was used to produce the title compound, substituting tetrahydrofuran for chloroform, triethylamine for diisopropylethylamine and benzoyl chloride for 4-bromobenzenesulfonyl chloride. The title compound was obtained as a solid with a melting point of about 103° to 106° C.
Elemental Analysis data for $C_{24}H_{14}NO_2Cl$ (335.777):

|  | Calculated |  | Found |
| --- | --- | --- | --- |
|  | 71.54 | C | 71.72 |
|  | 4.20 | H | 4.49 |
|  | 4.17 | N | 4.10 |
|  | 10.56 | Cl | 10.60 |

EXAMPLE 38

10-Benzoyl-8-trifluromethyl-dibenz[b,f][1,4]oxazepine

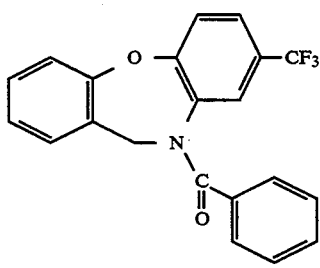

8-trifluoromethyl-dibenz[b,f]1,4]oxazepine is prepared in the manner described in U.S. Pat. No. 3,534,019.

Briefly, 200 parts of 4-chloro-3-nitrobenzotrifluoride is heated to 160° C. and stirred and 160 parts of the potassium salt of salicylaldehyde is added over a period of 30 minutes. After the addition is complete, an exothermic reaction takes place and the temperature rises to about 195° C. Heating is then discontinued until the reaction subsides and the mixture is then heated for 1 hour at 150° C. The mixture is cooled, ice and water are added, and it is then extracted with ether. The ether layer is filtered to remove insoluble material and the resultant solution is dried over sodium sulfate. The ether solvent is then evaporated and the residual oil is recrystallized from a mixture of hexane and benzene to give 2-(2-nitro-4-trifluoro-methylphenoxy)benzaldehyde melting at about 79°-81° C.

A solution of 55 parts of the ether obtained in the preceding paragraph in 800 parts of ethanol is hydrogenated over Raney nickel catalyst at room temperature and atmospheric pressure. When hydrogen uptake ceases the catalyst is removed by filtration and the ethanol solvent is evaporated. The residue is then dissolved in 500 parts by volume of hexane, filtered, and then cooled. There is then obtained yellowish-white crystals which are separated by filtration to give 8-trifluoromethyl-dibenz[b,f]1,4]oxazepine melting at about 86°-88° C.

The title compound is obtained by the method of Example 37, with the substitution of 8-trifluoromethyl-dibenz-[b,f][1,4]oxazepine for 4-bromobenzenesulphonyl chloride.

EXAMPLE 39

Methyl 2-[(8-chlorodibenz[b,f][1,4]oxazepin-10(11H)-yl)-carbonyl]-N-4-methylbenzoate

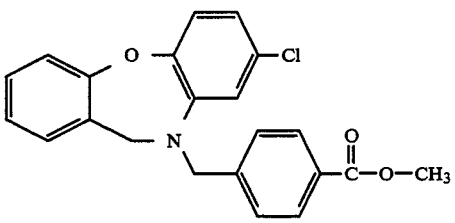

To a stirred solution of 8-chloro-10,11-dihydrodibenz[b,f][1,4]oxazepine (80 mg) in dimethyl formamide (1 mL) was added a 1 M solution of potassium tert-butoxide in tetrahydrofuran (0.43 mL), followed after 15 minutes by methyl 4-bromomethylbenzoate (121 mg). After stirring for 30 minutes, saturated aqueous ammonium chloride was added and the reaction mixture was concentrated and purified by chromatography on silica gel eluting with hexane and methylene chloride (1.5:1). The title compound was recovered as an oil: $^1H$ NMR (CDCl$_3$) δ3.93 (s, 3H), 4.40 (s, 2H), 4.43 (s, 2H), 6.72 (m, 2H), 7.05–7.12 (m, 3H), 7.19 (d, J=7.73 Hz, 1H), 7.26–7.33 (m, 1H), 7.42 (d, J=8.47 Hz, 2H), 8.04 (d, J=8.32 Hz, 2H); MS (FAB) m/e (relative intensity) 386 (78), 380 (21), 379 (44), 230 (72), 149 (65); HRMS. calculated for M+H: 386.1135. Found: 386.1154.

EXAMPLE 40

Methyl 2-[(8-chlorodibenz[b,f][1,4]oxazepin-10 (11H)-yl)carbonyl]-N-3-methylbenzoate

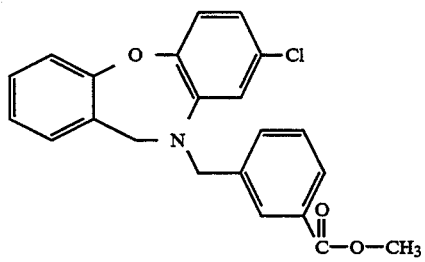

To a stirred solution of 8-chloro-10,11dihydrodibenz[b,f][1,4]oxazepine (80 mg) in dimethyl formamide (1 mL) was added a 1 M solution of potassium tert-butoxide in tetrahydrofuran (0.43 mL), followed after 15 minutes by methyl 2-bromomethylbenzoate (121 mg). After stirring for two hours, saturated aqueous ammonium chloride was added, and the reaction mixture was concentrated and purified by chromatography on silica gel eluting with hexane and ethyl acetate (12:1). The title compound was recovered in a 26% yield from the tricycle: $^1$H NMR (CDCl$_3$) δ3.93 (s, 3H), 4.38 (s, 2H), 4.40 (s, 2H), 6.74 (m, 2H), 7.07 (m, 3H), 7.18–7.36 (m, 2H), 7.45–7.59 (m, 2H), 8.0 (m, 2H); MS (FAB) m/e (relative intensity) 386 (70), 379 (100), 230 (75), 149 (96); HRMS. calculated for M+H: 386.1135. Found: 386.1143.

EXAMPLE 41

2-[(8-chlorodibenz[b,f][1,4]oxazepin-10(11H)-yl)carbonyl]-N-3-methylbenzoic acid

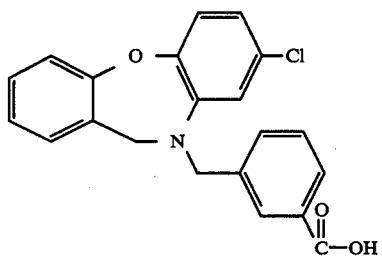

To a solution of the title compound from Example (25 rag) in tetrahydrofuran (0.5 mL) was added 2 M LiOH (0.5 mL), and the reaction mixture was stirred at room temperature overnight. The solvent was removed, the residue was diluted with water and acidified with 2 M HCl, and the title compound was collected as a precipitate: $^1$H NMR (CDCl$_3$) δ4.42 (s, 2H), 4.44 (s, H), 4.71 (bs, 1H), 6.77 (dd, J=8.54, 2.44 Hz, 1H), 6.83 (d, J=2.36, 1H), 7.07 (m, 3H), 7.19–7.35 (m, 2H), 7.50 (t, J=8.04 Hz, 1H), 7.66 (d, J=7.74 Hz, 1H), 8.07 (s, 2H); MS (FAB) m/e (relative intensity) (65), 230 (45); HRMS. calculated for M+H: 366.0897. Found: 366.0834.

EXAMPLE 42

Methyl 2-[(8-chlorodibenz[b,f][1,4]oxazepin-10(11H)-yl)-carbonyl]-N-benzyl-2-methylbenzoate

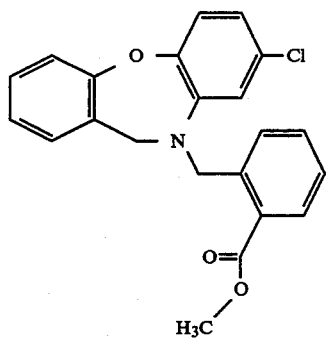

To a stirred solution of methyl 2-methylbenzoate (5.0 g) in carbon tetrachloride (500 mL) was added N-bromosuccinimide (7.1 g) and 2,2'-azobis-(2-methylpropionitrile) (0.7 g), and the reaction mixture was refluxed for 1.5 hours. The reaction mixture was washed with water, the water extracted with carbon tetrachloride, and the organic phase was dried over MgSO$_4$ and concentrated. The residue was purified by chromatography over silica gel eluting with hexane and methylene chloride (2:1). A mixture containing 86% of the monobromo product, and 14% of the starting material was recovered and used in the subsequent reaction: $^1$H NMR (CDCl$_3$) δ3.94 (s, 3H), 4.96 (s, 2H), 7.37–7.50 (m, 3H), 7.97 (d, 1H).

To a stirred solution of 8-chloro-10,11-dihydrodibenz[b,f][1,4]oxazepine (80 mg) in dimethyl formamide (1 mL) was added a 1 M solution of potassium tert-butoxide in tetrahydrofuran (0.43 mL), followed after 15 minutes by methyl 2-bromomethylbenzoate (141 mg, 86% pure). After stirring for two hours, saturated aqueous ammonium chloride was added and the reaction mixture was concentrated and purified by chromatography on silica gel eluting with hexane and ethyl acetate (12:1). The title compound was recovered pure in 48% yield: $^1$H NMR (CDCl$_3$) δ3.90 (s, 3H), 4.48 (s, 2H), 4.82 (s, 2H), 6.49 (d, J=2.43 Hz, 1H), 6.65 (dd, J=8.51, 2.44 Hz, 1H), 7.04–7.08 (m, 2H), 7.20 (d, J=8.01 Hz, 1H), 7.26–7.41 (m, 3H), 7.50 (m, 2H), 8.05 (d, J=7.46 Hz, 1H); MS (FAB) m/e (relative intensity) 386 (78), 348 (19), 230 (72), 149 (66); HRMS. calculated for M+H: 386. 1135. Found: 386. 1140.

EXAMPLE 43

2-[(8-chlorodibenz[b,f][1,4]oxazepin-10(11H)-yl)carbonyl]-N-benzyl-2-carboxylate

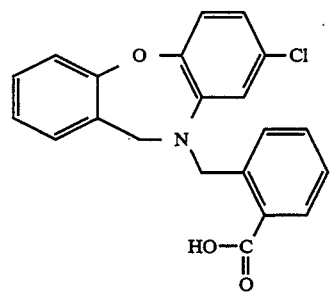

To a solution of the title compound of Example 42 (50 mg) in tetrahydrofuran (0.5 mL) was added 2 M LiOH (0.5 mL), and the reaction mixture was warmed to 80° C. for 1.5 hours. The solvent was removed, the residue was diluted with water, acidified with 2 M HCl, and the title compound was collected as a precipitate: $^1$H NMR (CDCl$_3$) δ4.47 (s, 2H), 4.74 (s, 2H), 6.69 (d, J=2.24 Hz, 1H), 6.79 (dd, J=8.54, 2.36 Hz, 1H), 7.09 (m, 3H), 7.20–7.32 (m, 2H), 7.38–7.47 (m, 2H), 7.52–7.54 (m, 1H), 8.17 (d, J=7.85 Hz, 1H); MS (FAB) m/e (relative intensity) 366 (34), 230 (56); HRMS. calculated for M+H: 366. 0897. Found: 366.0863.

The foregoing examples are provided to enable one of ordinary skill in the art to practice the present invention. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131–140 (1984); C. Vander Wende et al., Fed. Proc., 15, 494 (1956); Koster et al., Fed. Proc., 18, 412 (1959); and Witken et al., J. Pharmacol. exp. Ther., 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 1 hereinbelow.

Charles River male albino mice, weighing 20 to 30 grams were used in this assay.

Twenty-five minutes after intragastric administration to nine or ten mice of 10 or 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 10 or 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," Advances in Biochemical Psychopharmacology, 8, 191 (1974).

The standard initial screening dose of a test compound employed in this assay was 10 (for those compounds shown and described in Example 8, Compounds E and F, and Example 9 by an intragastric mode of administration) or 30 (for all of the other compounds tested in this assay) mpk per gram of body weight.

The results for the particular compounds of the present invention analyzed in this assay, and discussed in the examples identified below which correspond thereto, are presented in Table 1 hereinbelow under the heading "WRITHING ASSAY." The fractions indicate the number of mice out of nine or ten in which a test compound produced analgesia.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio of $EC_{50}$ doses was then calculated from the results of each test in a manner known by those of skill in the art.

The results of this prostaglandin antagonism assay are also presented in Table 1 below. The compounds of the present invention which were tested in this assay, and for which results are presented in Table 1, correspond to the particular examples specified in Table 1.

TABLE 1

| | Data Generated from the Assays | |
|---|---|---|
| Example Number | WRITHING ASSAY Number Out of Nine or Ten | PGE ANTAGONISM IN GUINEA PIG ILEUM Dose Ratio (DR) |
| Example 3 | 5/10 | 1.0 |
| Example 4 | 6/10 | Cellular Receptors Blocked |
| Example 5 | 3/10 | 4.4 |
| Example 8, Compound E | 9/10 | 4.8 |
| Example 8, Compound F | 9/10 | 1.1 |
| Example 9 | 8/10 | 2.29 |
| Example 10 | 4/10 | 3.2 |
| Example 12 | 3/9 | 4.23 |
| Example 13 | 5/10 | 1.10 |
| Example 14 | 3/10 | 4.07 |
| Example 16 | 8/10 | 4.67 |
| Example 17 | 5/10 | 66.0 |
| Example 18 | 7/10 | 114 |
| Example 19 | 5/10 | 0.44 |
| Example 20 | 8/10 | * |
| Example 21 | 4/10 | 1.9 |
| Example 22 | 8/10 | 2.13 |
| Example 24 | 3/10 | 5.86 |
| Example 25 | 5/10 | 0.69 |
| Example 26 | 8/10 | 0.4 |
| Example 27 | 5/10 | 22.7 |
| Example 28 | 6/10 | 3.59 |
| Example 29 | 5/10 | 10.4 |
| Example 30 | 7/10 | 0.81 |
| Example 31 | 6/10 | 1.70 |
| Example 32 | 3/10 | 0.63 |
| Example 34 | 2/10 | 1.16 |
| Example 35 | 7/10 | * |
| Example 36 | 7/9 | 2.6 |

* - Not tested.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound having a structure:

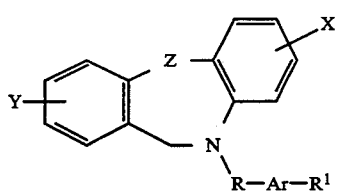

or a pharmaceutically-acceptable salt thereof, wherein:
X is hydrogen, halogen or —CF₃;
Y is hydrogen or halogen;
Z is oxygen, sulfur,

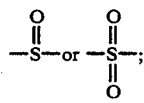

R is

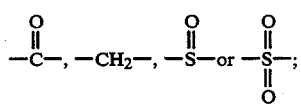

Ar is aryl; and
R¹ is hydrogen, halogen, aryl, alkylaryl, alkenylaryl, alkynylaryl, carboxy, carbonylalkoxy or carbonylaminoalkylaryl,
with the proviso that R is not —CH₂— when R¹ is carboxy, phenyl or alkylphenyl.

2. A compound of claim 1 wherein R¹ is

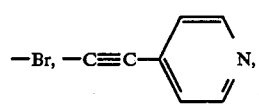

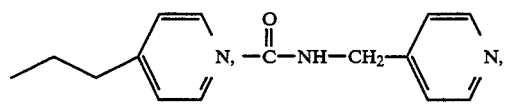

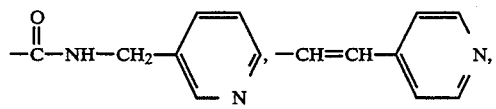

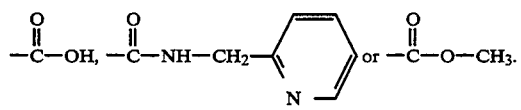

3. A compound of claim 2 wherein Ar is

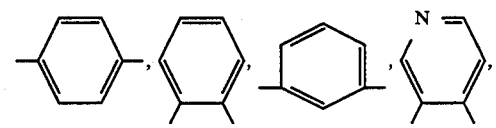

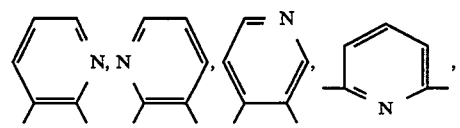

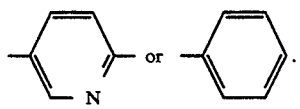

4. A compound of claim 3 wherein Z is oxygen.

5. A compound of claim 4 wherein X is halogen or —CF₃.

6. A compound of claim 5 wherein Y is hydrogen.

7. A compound of claim 6 wherein X is chlorine or —CF₃.

8. A compound of claim 1, wherein the compound is:

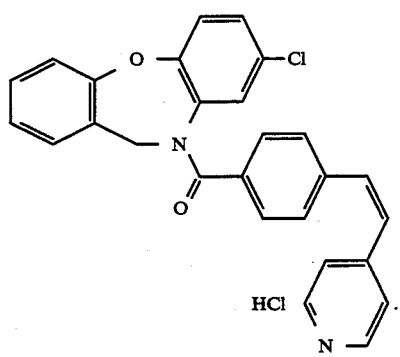

9. A compound of claim 1, wherein the compound is:

10. A compound of claim 1, wherein the compound is:
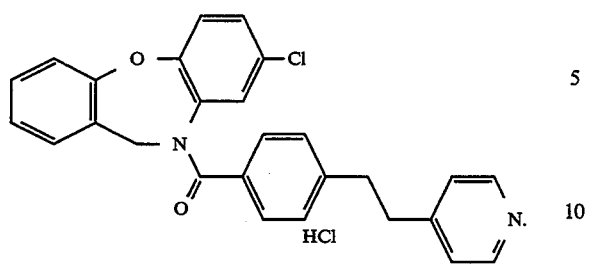
11. A compound of claim 1, wherein the compound is:
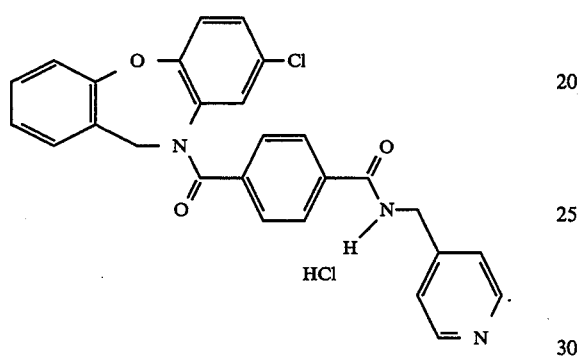
12. A compound of claim 1, wherein the compound is:
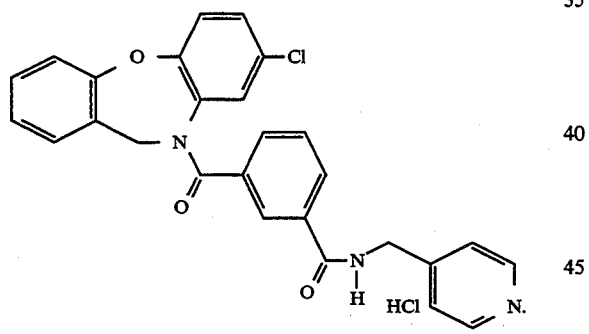
13. A compound of claim 1, wherein the compound is:
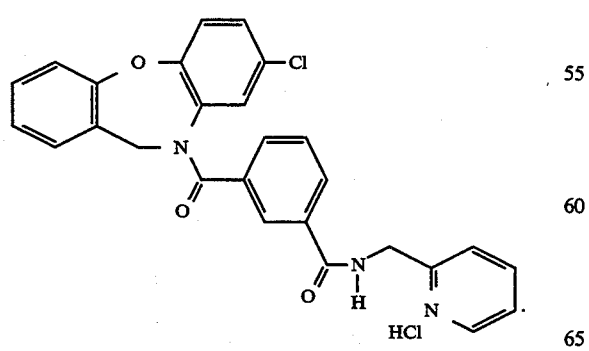
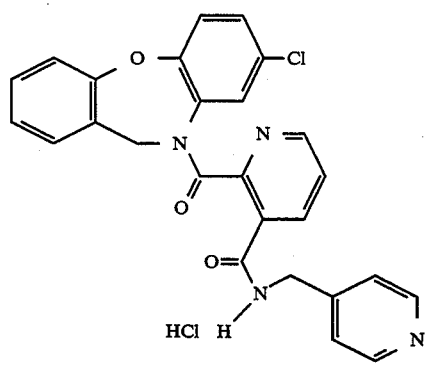
or
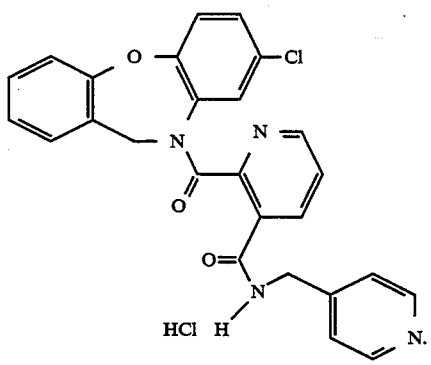
14. A compound of claim 1, wherein the compound is:
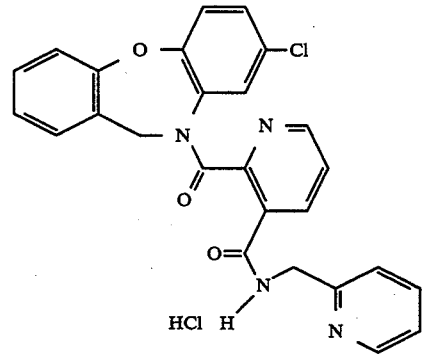
or
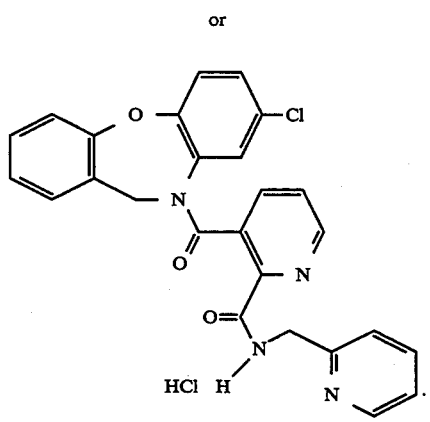

15. A compound of claim 1, wherein the compound is:

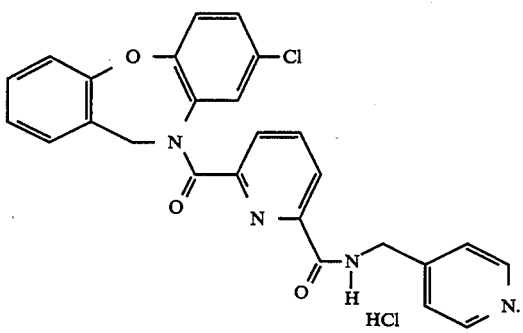

16. A compound of claim 1, wherein the compound is:

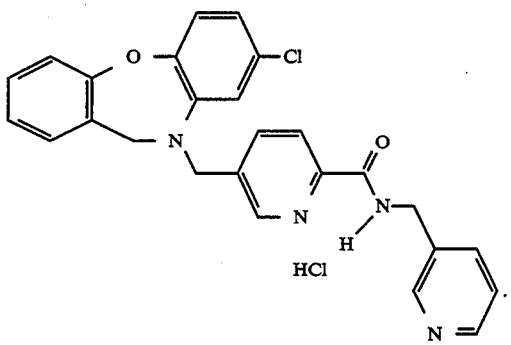

17. A compound of claim 1, wherein the compound is:

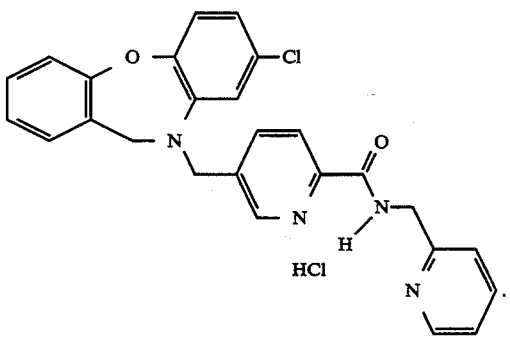

18. A compound of claim 1, wherein the compound is: 8-chloro-10,11-dihydro-10-[[[4-[2-(4-pyridinyl)ethyl]phenyl]sulfonyl]dibenz[b,f][1,4]-oxazepine, monohydrochloride;
  4-[(8-chlorodibenz[b,f][1,4]oxazepin-10(11H)-yl)sulfonyl]-N-(4-pyridinylmethyl)benzamide, monohydrochloride;
  4-[(8-chlorodibenz[b,f][1,4]oxazepin-10(11H)-yl)sulfonyl]-N-(3-pyridinylmethyl)benzamide, monohydrochloride;
  8-chloro-10,11-dihydro-10-[4-[2Z-(4-pyridinyl)ethenyl]benzoyl]dibenz[b,f][1,4]oxazepine, hydrochloride;
  8-chloro-10,11-dihydro-10-[4-[2-(4-pyridinyl)ethyl]benzoyl]dibenz[b,f][1,4]oxazepine, hydrochloride;

4-[(8-chlorodibenz[b,f][1,4]oxazepin-10(11H)-yl)carbonyl]-N-(4-pyridinylmethyl)benzamide, hydrochloride;
4-[(8-chlorodibenz[b,f][1,4]oxazepin-10(11H)-yl)carbonyl]-N-(3-pyridinylmethyl)benzamide, hydrochloride;
2-[(8-chlorodibenz[b,f][1,4]oxazepin-10(11H)-yl)carbonyl]-N-(4-pyridinylmethyl)benzamide, hydrochloride;
2-(8-chlorodibenz[b,f][1,4]oxazepin-10(11H)-yl)carbonyl]-N-(3-pyridinylmethyl)benzamide, hydrochloride;
2-[(8-chlorodibenz[b,f][1,4]oxazepin-10(11H)-yl)carbonyl]-N-(2-pyridinylmethyl)benzamide, dihydrochloride;
3-[(8-chlorodibenz[b,f][1,4]oxazepin-10(11H)-yl)carbonyl]-N-(4-pyridinylmethyl)benzamide, monohydrochloride;
3-[(8-chlorodibenz[b,f][1,4]oxazepin-10(11H)-yl )carbonyl]-N-(3-pyridinylmethyl)benzamide, monohydrochloride;
3-[(8-chlorodibenz[b,f][1,4]oxazepin-10(11H)-yl )carbonyl]-N-(2 -pyridinylmethyl)benzamide, hydrochloride;
2-[(8-chlorodibenz[b,f][1,4]oxazepin-10(11H)-yl)carbonyl]amino]-3-pyridinecarboxylic acid;
3-[(8-chlorodibenz[b,f][1,4]oxazepin-10(11H)-yl)carbonyl]-2-pyridinecarboxylic acid;
2-[(8-chlorodibenz[b,f][1,4]oxazepin-10(11H)-yl)carbonyl]-N-(4-pyridinylmethyl)-3-pyridinecarboxamide, dihydrochloride;
3-[(8-chlorodibenz[b,f][1,4]oxazepin-10(11H)-yl)carbonyl]-N-(4-pyridinylmethyl)-2-pyridinecarboxamide, monohydrochloride;
2-[(8-chlorodibenz[b,f][1,4]oxazepin-10(11H)-yl)carbonyl]-N-(3-pyridinylmethyl)-3-pyridinecarboxamide, dihydrochloride;
3-[(8-chlorodibenz[b,f][1,4]oxazepin-10(11H)-yl)carbonyl]-N-(3-pyridinylmethyl)-2-pyridinecarboxamide;
2-[(8-chlorodibenz[b,f][1,4]oxazepin-10(11H)-yl)carbonyl]-N-(2-pyridinylmethyl)-3-pyridinecarboxamide, dihydrochloride;
3-[(8-chlorodibenz[b,f][1,4]oxazepin-10(11H)-yl)carbonyl]-N-(2-pyridinylmethyl)-2-pyridinecarboxamide, monohydrochloride;
4-[(8-chlorodibenz[b,f][1,4]oxazepin-10(11H)-yl)carbonyl]-N-(4-pyridinylmethyl)-3-pyridinecarboxamide, dihydrochloride;
3-[(8-chlorodibenz[b,f][1,4]oxazepin-10(11H)-yl)carbonyl]-N-(4-pyridinylmethyl)-4-pyridinecarboxamide, monohydrochloride;
4-[(8-chlorodibenz[b,f][1,4]oxazepin-10(11H)-yl)carbonyl]-N-(3-pyridinylmethyl)-3-pyridinecarboxamide, hydrochloride;
3-[(8-chlorodibenz[b,f][1,4]oxazepin-10(11H)-yl)carbonyl]-N(3-pyridinylmethyl)-4-pyridinecarboxamide, monohydrochloride;
4-[(8-chlorodibenz[b,f][1,4]oxazepin-10(11H)-yl)carbonyl]-N-(3-pyridinylmethyl )-3-pyridinecarboxamide, hydrochloride;
3-[(8-chlorodibenz[b,f][1,4]oxazepin-10(11H)-yl)carbonyl]-N-(2-pyridinylmethyl)-4-pyridinecarboxamide, monohydrochloride;
4-[(8-chlorodibenz[b,f][1,4]oxazepin-10(11H)-yl)methyl]-N-(3-pyridinylmethyl)benzamide, hydrochloride;

4-[(8-chlorodibenz[b,f][1,4]oxazepin-10(11H)-yl)methyl]-N-(3-pyridinylmethyl)benzamide, hydrochloride;

4-[(8-chlorodibenz[b,f][1,4]oxazepin-10(11H)-yl)methyl]-N-(2-pyridinylmethyl)benzamide, hydrochloride;

6-[(8-chlorodibenz[b,f][1,4]oxazepin-10(11H)-yl)carbonyl]-N-(4-pyridinylmethyl)-2-pyridinecarboxamide, hydrochloride;

6-[(8-chlorodibenz[b,f][1,4]oxazepin-10(11H)-yl)carbonyl]-N-(3-pyridinylmethyl)-2-pyridinecarboxamide, hydrochloride;

6-[(8-chlorodibenz[b,f][1,4]oxazepin-10(11H)-yl)carbonyl]-N-(2-pyridinylmethyl)-2-pyridinecarboxamide, hydrochloride;

5-[(8-chlorodibenz[b,f][1,4]oxazepin-10(11H)-yl)methyl]-N-(4-pyridinylmethyl)-2-pyridinecarboxamide, monohydrochloride;

5-[(8-chlorodibenz[b,f][1,4]oxazepin-10(11H)-yl)methyl]-N-(3-pyridinylmethyl)-2-pyridinecarboxamide, monohydrochloride;

5-[(8-chlorodibenz[b,f][1,4]oxazepin-10(11H)-yl)methyl]-N-(2-pyridinylmethyl)-2-pyridinecarboxamide, monohydrochloride; or 10-(Benzoyl)-8-chloro-10,11-dihydrodibenz[b,f][1,4]oxazepine.

* * * * *

UNITED STATES PATENT AND TRADEMARK OFFICE
CERTIFICATE OF CORRECTION

PATENT NO. : 5,420,270          Page 1 of 2
DATED      : May 30, 1995
INVENTOR(S): Chandrakumar, et al.

It is certified that error appears in the above-indentified patent and that said Letters Patent is hereby corrected as shown below:

Column 10, line 55, reading "6membered" should read --6-membered--.

Column 20, line 40, reading "(0,116 g)" should read --(0.116 g)--.

Column 20, line 41, reading "(0,006 g)" should read --(0.006 g)--.

Column 23, lines 64 & 65, reading "using ethyl" should read --using 60% ethyl--.

Column 26, line 29, reading "for hours" should read --for 16 hours--.

Column 32, line 4, reading "[1,4-oxazepin" should read --[1,4]oxazepin--.

Column 32, line 25, reading "3(aminomethyl)" should read --3-(aminomethyl)--.

Column 41, line 28, reading "(11H)yl)" should read --(11H)-yl)--.

Column 41, line 47, reading "(0,658 g)" should read --(0.658 g)--.

Column 43, line 22, reading "$C_{24}H_{14}$" should read --$C_{20}H_{14}$--.

Column 44, lines 61 & 62, reading "11dihydrodibenz" should read --11-dihydrodibenz--.

Column 45, line 26, reading "Example (25 rag)" should read --Example 40 (25 mg)--.

Column 45, line 32, reading "(s, H)" should read --(s, 2H)--.

UNITED STATES PATENT AND TRADEMARK OFFICE
CERTIFICATE OF CORRECTION

PATENT NO. : 5,420,270
DATED : May 30, 1995
INVENTOR(S) : Chandrakumar, et al.

It is certified that error appears in the above-indentified patent and that said Letters Patent is hereby corrected as shown below:

Column 45, line 36, reading "(65)" should read --366 (65)--.

Column 47, line 22, reading "0,025%" should read --0.025%--.

Signed and Sealed this

Seventeenth Day of June, 1997

Attest:

BRUCE LEHMAN

Attesting Officer

Commissioner of Patents and Trademarks